United States Patent
Berthiaume et al.

(10) Patent No.: US 11,135,218 B2
(45) Date of Patent: Oct. 5, 2021

(54) SYNTHETIC LETHALITY AND THE TREATMENT OF CANCER

(71) Applicant: PACYLEX PHARMACEUTICALS INC., Calgary (CA)

(72) Inventors: Luc G. Berthiaume, Edmonton (CA); Erwan Beauchamp, Rennes (FR); Conganige Maneka Anne Perinpanayagam, Edmonton (CA); Chuiyee Yap, Edmonton (CA)

(73) Assignee: PACYLEX PHARMACEUTICALS INC., Edmonton (CA)

( * ) Notice: Subject to any disclaimer, the term of this patent is extended or adjusted under 35 U.S.C. 154(b) by 0 days.

(21) Appl. No.: 16/025,835

(22) Filed: Jul. 2, 2018

(65) Prior Publication Data
US 2019/0000838 A1    Jan. 3, 2019

Related U.S. Application Data

(63) Continuation of application No. 14/234,312, filed as application No. PCT/CA2012/000696 on Jul. 23, 2012, now abandoned.

(60) Provisional application No. 61/510,686, filed on Jul. 22, 2011.

(51) Int. Cl.
| | |
|---|---|
| *A61K 31/496* | (2006.01) |
| *A61K 31/713* | (2006.01) |
| *A61K 31/191* | (2006.01) |
| *A61K 31/28* | (2006.01) |
| *A61K 31/7105* | (2006.01) |
| *A61K 31/12* | (2006.01) |
| *A61K 45/06* | (2006.01) |
| *G01N 33/574* | (2006.01) |
| *C07K 16/40* | (2006.01) |
| *C12Q 1/686* | (2018.01) |
| *G01N 33/50* | (2006.01) |

(52) U.S. Cl.
CPC ............ *A61K 31/496* (2013.01); *A61K 31/12* (2013.01); *A61K 31/191* (2013.01); *A61K 31/28* (2013.01); *A61K 31/713* (2013.01); *A61K 31/7105* (2013.01); *A61K 45/06* (2013.01); *C07K 16/40* (2013.01); *C12Q 1/686* (2013.01); *G01N 33/5091* (2013.01); *G01N 33/574* (2013.01); *G01N 33/57496* (2013.01)

(58) Field of Classification Search
None
See application file for complete search history.

(56) References Cited

U.S. PATENT DOCUMENTS

| | | | |
|---|---|---|---|
| 5,164,414 | A | 11/1992 | Vincent et al. |
| 7,449,464 | B2 | 11/2008 | Martin et al. |
| 7,662,818 | B2 | 2/2010 | Martin et al. |
| 7,981,889 | B2 | 7/2011 | Barr Martin et al. |
| 2003/0180292 | A1 | 9/2003 | Hanna et al. |
| 2005/0227919 | A1 | 10/2005 | Ashworth et al. |
| 2006/0142231 | A1 | 6/2006 | Ashworth et al. |
| 2007/0179160 | A1 | 8/2007 | Helleday |
| 2010/0068731 | A1 | 3/2010 | Sharma et al. |
| 2011/0312921 | A1 | 12/2011 | Brand et al. |
| 2018/0208990 | A1 | 7/2018 | Berthiaume et al. |

FOREIGN PATENT DOCUMENTS

| | | |
|---|---|---|
| AU | 2004220321 B2 | 2/2010 |
| AU | 2010202197 A1 | 6/2010 |
| BR | PI0408284 A | 3/2006 |
| BR | PI0417056 A | 2/2007 |
| BR | 112014001430 A2 | 2/2017 |
| CA | 2547077 A1 | 6/2005 |
| CA | 2670837 A1 | 6/2008 |
| CA | 2517629 C | 7/2011 |
| CN | 101631466 A | 1/2010 |
| CN | 1788000 B | 7/2010 |
| CN | 1905864 B | 4/2011 |
| CN | 102107008 A | 6/2011 |
| CO | 5650256 A2 | 6/2006 |
| DK | 1633724 T3 | 8/2011 |
| EC | SP056094 A | 3/2006 |
| EP | 2305221 A1 | 4/2011 |
| EP | 1633724 B1 | 5/2011 |
| EP | 1684736 B1 | 8/2011 |
| ES | 2364140 T3 | 8/2011 |
| IS | 8052 A | 9/2005 |
| JP | H04210916 A | 8/1992 |

(Continued)

OTHER PUBLICATIONS

Ducker et al. "Two N-Myristoyltransferase Isozymes Play Unique Roles in Protein Myristoylation, Proliferation, and Apoptosis," Mol. Cancer Res. 2005; 3(8). Aug. 2005 463-476 (Year: 2005).*
UNIPROT, NMT2_HUMAN: Protein Glycylpeptide N-tetradecanoyltransferase 2; Gene NMT2. Accessed online at http://www.uniprot.org/uniprot/060551 on Mar. 10, 2017, 11 pages.
U.S. Appl. No. 14/234,312, Final Office Action dated Aug. 24, 2016.
U.S. Appl. No. 14/234,312, Final Office Action dated Jan. 12, 2018.
U.S. Appl. No. 14/234,312, Non-Final Office Action dated Mar. 31, 2017.
U.S. Appl. No. 14/438,594, Final Office Action dated Oct. 2, 2017.
U.S. Appl. No. 14/438,594, Non-Final Office Action dated Mar. 22, 2017.

(Continued)

*Primary Examiner* — Jeffrey S Lundgren
*Assistant Examiner* — Michael J Schmitt
(74) *Attorney, Agent, or Firm* — Acuity Law Group, PC; Michael A. Whittaker

(57) ABSTRACT

Described herein are compounds, compositions and methods for treatment of cancer. Also described are methods and uses for identifying subject with cancer that are suitable for treatment with the compounds, composition and methods are described herein. In one aspect of the present invention, there is provided a method of treating a subject having a cancer deficient in NMT2, comprising: administering to said subject an NMT inhibitor.

6 Claims, 7 Drawing Sheets

(56) References Cited

FOREIGN PATENT DOCUMENTS

| | | |
|---|---|---|
| JP | 2007516241 A | 6/2007 |
| JP | 2007520557 A | 7/2007 |
| JP | 4027406 B2 | 12/2007 |
| JP | 2009079056 A | 4/2009 |
| JP | 4268651 B2 | 5/2009 |
| JP | 6270719 B2 | 1/2018 |
| KR | 102164964 B1 | 10/2020 |
| MA | 27758 A1 | 2/2006 |
| MX | PA05009661 A | 3/2006 |
| NO | 20054625 A | 11/2005 |
| NZ | 542680 A | 8/2008 |
| NZ | 547984 A | 3/2009 |
| PT | 1633724 E | 7/2011 |
| RU | 2413515 C2 | 3/2011 |
| SI | 1633724 T1 | 9/2011 |
| WO | 2004080976 A1 | 9/2004 |
| WO | 2005012305 A2 | 2/2005 |
| WO | 2005012524 A1 | 2/2005 |
| WO | 2005053662 A1 | 6/2005 |
| WO | 2005076843 A2 | 8/2005 |
| WO | 2006014729 A2 | 2/2006 |
| WO | 2006086043 A2 | 8/2006 |
| WO | 2008076965 A1 | 6/2008 |
| WO | 2010026365 A1 | 3/2010 |
| WO | 2013013302 A1 | 1/2013 |
| WO | 2014067002 A1 | 5/2014 |

OTHER PUBLICATIONS

Uno et al., "Myristoylation of the Fus1 Protein Is Required for Tumor Suppression in Human Lung Cancer Cells," Cancer Research, May 2004, vol. 64 (9), pp. 2969-2976.

Utsumi et al., "C-Terminal 15 kDa Fragment of Cytoskeletal Actin is Posttranslationally N-Myristoylated Upon Caspase-Mediated Cleavage and Targeted to Mitochondria," FEBS Letters, Mar. 2003, vol. 539 (1-3), pp. 37-44.

Utsumi et al., "Vertical-Scanning Mutagenesis of Amino Acids in a Model N-Myristoylation Motif Reveals the Major Amino-Terminal Sequence Requirements for Protein N-Myristoylation," European Journal of Biochemistry, Feb. 2004, vol. 271 (4), pp. 863-874.

Veer et al., "Enabling Personalized Cancer Medicine Through Analysis of Gene-Expression Patterns," Nature, Apr. 2008, vol. 452 (7187), pp. 564-570.

Vilas et al., "Posttranslational Myristoylation of Caspase'activated P21-Activated Protein Kinase 2 (PAK2) Potentiates Late Apoptotic Events," Proceedings of the National Academy of Sciences of the United States of America, Apr. 2006, vol. 103 (17), pp. 6542-6547.

Wahlstrom et al., "Rce1 Deficiency Accelerates the Development of K-RAS-induced Myeloproliferative Disease," Blood, Jan. 2007, vol. 109 (2), pp. 763-768.

Walsh et al., "Executioner Caspase-3 and Caspase-7 Are Functionally Distinct Proteases," Proceedings of the National Academy of Sciences of the United States of America, Sep. 2008, vol. 105 (35), pp. 12815-12819.

Wang et al., "Bioconjugation by Copper(I)-Catalyzed Azide-Alkyne [3+2] Cycloaddition," Journal of the American Chemical Society, Mar. 2003, vol. 125 (11), pp. 3192-3193.

Webb et al., "Inhibition of Protein Palmitoylation, Raft Localization, and T Cell Signaling by 2-bromopalmitate and Polyunsaturated Fatty Acids," The Journal of Biological Chemistry, Jan. 2000, vol. 275 (1), pp. 261-270.

Weinberg et al., "Genetic Studies Reveal that MyristoylCoA:protein N-Myristoyltransferase is an Essential Enzyme in Candida Albicans," Molecular Microbiology, Apr. 1995, vol. 16 (2), pp. 241-250.

Weston et al., "Crystal Structure of the Anti-Fungal Target N-Myristoyl Transferase," Nature Structural Biology, Mar. 1998, vol. 5 (3), pp. 213-221.

Wikipedia, Definition: Small molecule. Accessed online at https://en.wikipedia.org.wiki/Small_molecule on Mar. 10, 2017, 4 pages.

Wilcox et al., "Acylation of Proteins With Myristic Acid Occurs Cotranslationally," Science, Nov. 1987, vol. 238 (4831), pp. 1275-1278.

Willert et al., "Wnt Proteins are Lipid-Modified and can Act as Stem Cell Growth Factors," Nature, May 2003, vol. 423 (6938), pp. 448-452.

Wright et al., "Protein Myristoylation in Health and Disease," Journal of Chemical Biology, Mar. 2010, vol. 3 (1), pp. 19-35.

Written Opinion for Application No. PCT/CA2012/000696, dated Nov. 7, 2012, 7 pages.

Written Opinion for Application No. PCT/CA2013/050821, dated Feb. 5, 2014, 8 pages.

Wu et al., "Crystal Structures of *Saccharomyces cerevisiae* N-myristoyltransferase With Bound Myristoyl-CoA and Inhibitors Reveal the Functional Roles of the N-Terminal Region," The Journal of Biological Chemistry, Jul. 2007, vol. 282 (30), pp. 22185-22194.

Wu et al., "Necroptosis: An Emerging Form of Programmed Cell Death," Critical Reviews in Oncology/hematology, Jun. 2012, vol. 82 (3), pp. 249-258.

Yang et al., "Identification of the Acyltransferase that Octanoylates Ghrelin, an Appetite-Stimulating Peptide Hormone," Cell, Feb. 2008, vol. 132 (3), pp. 387-396.

Yang et al., "N-Myristoyltransferase 1 Is Essential in Early Mouse Development," The Journal of Biological Chemistry, May 2005, vol. 280 (19), pp. 18990-18995.

Yap et al., "Rapid and Selective Detection of Fatty Acylated Proteins Using Omega-Alkynyl-Fatty Acids and Click Chemistry," Clinical Cancer Research, Jun. 2010, vol. 51 (6), pp. 1566-1580.

Youle et al., "The BCL-2 Protein Family: Opposing Activities that Mediate Cell Death," Nature Reviews Molecular Cell Biology, Jan. 2008, vol. 9 (1), pp. 47-59.

Yustein et al., "Biology and Treatment of Burkitt's Lymphoma," Current Opinion in Hematology, Jul. 2007, vol. 14 (4), pp. 375-381.

Zha, "Posttranslational N-Myristoylation of BID as a Molecular Switch for Targeting Mitochondria and Apoptosis," Science, Dec. 2000, vol. 290 (5497), pp. 1761-1765.

Zhang et al., "Down-Regulation of NKD1 Increases the Invasive Potential of Non-Small-Cell Lung Cancer and Correlates with a Poor Prognosis," BMC Cancer, May 2011, vol. 11, pp. 186.

Zhang et al., "Protein Prenylation: Molecular Mechanisms and Functional Consequences," Annual Review of Biochemistry, 1996, vol. 65, pp. 241-269.

Zhao et al, "Palmitoylation of Apolipoprotein B Is Required for Proper Intracellular Sorting and Transport of Cholesteroyl Esters and Triglycerides," Molecular Biology of the Cell, Feb. 2000, vol. 11 (2), pp. 721-734.

Zvernia et al., "Recent Advances in Protein Prenyltransferases: Substrate Identification, Regulation, and Disease-Interventions," Current Opinion in Chemical Biology, Dec. 2012, vol. 16 (5-6), pp. 544-552.

Canadian Patent Application No. 2,842,443, Office Action dated Jan. 28, 2019.

European Patent Application No. 13852049.9, Office Action dated Nov. 20, 2018.

Korean Patent Application No. 10-2014-7004635, Office Action dated Oct. 16, 2018.

Mexican Patent Application No. MX/a/2015/005441, Office Action dated Dec. 7, 2018—English Translation Not Available.

New Zealand Patent Application No. 707090, Office Action dated Nov. 13, 2018.

Russian Patent Application No. 2015118294, Notice of Allowance dated Oct. 23, 2018—English Translation Available.

Aitken et al., "Identification of the NH2-Terminal Blocking Group of Calcineurin B as Myristic Acid," FEBS Letters, Dec. 1982, vol. 150 (2), pp. 314-318.

Alizadeh et al., "Distinct Types of Diffuse Large B-Cell Lymphoma Identified by Gene Expression Profiling," Nature, Feb. 2000, vol. 403 (6769), pp. 503-511.

Alland et al., "Dual Myristylation and Palmitylation of Src Family Member P59fyn Affects Subcellular Localization," Journal of Biological Chemistry, Jun. 1994, vol. 269 (24), pp. 16701-16705.

(56) References Cited

OTHER PUBLICATIONS

Armah et al., "S-Myristoylation of a Glycosylphosphatidylinositol-Specific Phospholipase C in Trypanosoma Brucei," The Journal of Biological Chemistry, Feb. 1999, vol. 274 (9), pp. 5931-5938.
Ashworth et al., "A Synthetic Lethal Therapeutic Approach: Poly(ADP) Ribose Polymerase Inhibitors for the Treatment of cancers Deficient in DNA Double-Strand Break Repair," Journal of Clinical Oncology, Aug. 2008, vol. 26 (22), pp. 3785-3790.
Australian Patent Application No. 2012286542, Office Action dated Apr. 5, 2018.
Australian Patent Application No. 2012286542, Office Action dated Apr. 27, 2017.
Australian Patent Application No. 2013337569, Examination Report dated May 16, 2017.
Barneda-Zahonero et al., "Histone Deacetylases and Cancer," Molecular Oncology, Dec. 2012, vol. 6 (6), pp. 579-589.
Barretina et al., "The Cancer Cell Line Encyclopedia Enables Predictive Modelling of Anticancer Drug Sensitivity," Nature, Mar. 2012, vol. 483 (7391), pp. 603-607.
Bereshchenko et al., "Acetylation Inactivates the Transcriptional Repressor BCL6," Nature Genetics, Decembre 2002, vol. 32 (4), pp. 606-613.
Berndt et al., "Targeting Protein Prenylation for Cancer Therapy," Nature Reviews Cancer, Oct. 2011, vol. 11 (11), pp. 775-791.
Berthiaume et al., "Synthesis and Use of Iodo-Fatty Acid Analogs," Methods in Enzymology, 1995, vol. 250, pp. 454-466.
Beveridge et al., "Economic Impact of Disease Progression in Follicular Non-Hodgkin Lymphoma," Leukemia and Lymphoma, Nov. 2011, vol. 52 (11), pp. 2117-2123.
Bhandarkar et al., "Tris (Dibenzylideneacetone) Dipalladium, a N-Myristoyltransferase-1 Inhibitor, is Effective Against Melanoma Growth in Vitro and in Vivo," Clinical Cancer Research, Sep. 2008, vol. 14 (18), pp. 5743-5748.
Bhatnagar et al., "Isothermal Titration Calorimetric Studies of *Saccharomyces cerevisiae* Myristoyl-CoAProtein N-Vlyristoyltransfera. Determinants of Binding Energy and Catalytic Discrimination among ACYL-CoA and Peptide _igands," Journal of Biological Chemistry, Apr. 1994, vol. 269 (15), pp. 11045-11053.
Bhatnagar et al., "The Structure of Myristoyl-CoA:Protein N-Myristoyltransferase," Biochimica Et Biophysica Acta, Nov. 1999, vol. 1441 (2-3), pp. 162-172.
Bhatnagar et al., "Structure of N-Myristoyltransferase With Bound Myristoylcoa and Peptide Substrate Analogs," Nature Structural Biology, Dec. 1998, vol. 5 (12), pp. 1091-1097.
Boisson et al., "Unexpected Protein Families Including Cell Defense Components Feature in the N-Myristoylome of a Higher Eukaryote," Journal of Biological Chemistry, Oct. 2003, vol. 278 (44), pp. 43418-43429.
Bokoch, "Biology of the p21-Activated Kinases," Annual Review of Biochemistry, 2003, vol. 72, pp. 743-781.
Bologna et al., "N-Terminal Myristoylation Predictions by Ensembles of Neural Networks," Proteomics, Jun. 2004, vol. 4 (6), pp. 1626-1632.
Bosch, "Is Endemic Burkitt's Lymphoma an Alliance Between Three Infections and a Tumour Promoter?," The Lancet Oncology, Dec. 2004, vol. 5 (12), pp. 738-746.
Boutin et al., "Myristoylation," Cell Signal, Jan. 1997, vol. 9 (1), pp. 15-35.
Bowyer et al., "N-Myristoyltransferase: a Prospective Drug Target for Protozoan Parasites," ChemMedChem, Mar. 2008, vol. 3 (3), pp. 402-408.
Brady et al., "Epstein-Barr Virus and Burkitt Lymphoma," Journal of Clinical Pathology, Dec. 2007, vol. 60 (12), pp. 1397-1402.
Brannigan et al., "N-Myristoyltransferase from Leishmania donovani: Structural and Functional Characterisation of a Potential Drug Target for Visceral Leishmaniasis," Journal of Molecular Biology, Mar. 2010, vol. 396 (4), pp. 985-999.
Bratton et al., "Apoptotic Death Sensor: an Organelle's Alter Ego?," Trends in Pharmacological Sciences, Jun. 2001, vol. 22 (6), pp. 306-315.
Bryant et al., "Myristoylation-Dependent Replication and Assembly of Human Immunodeficiency Virus," Proceedings of the National Academy of Sciences of the United States of America, Jan. 1990, vol. 87 (2), pp. 523-527.
Bryant et al., "Specific Killing of BRCA2-deficient Tumours With Inhibitors of Poly(ADP-'ribose) Polymerase," Nature, Apr. 2005, vol. 434 (7035), pp. 913-917.
Buglino et al., "Hhat Is a Palmitoylacyltransferase with Specificity for N-Palmitoylation of Sonic Hedgeho," Journal of Biological Chemistry, Aug. 2008, vol. 283 (32), pp. 22076-22088.
Buglino et al., "Palmitoylation of Hedgehog Proteins," Vitamins and Hormones, 2012, vol. 88, pp. 229-252.
Burkitt, "A Sarcoma Involving the Jaws in African Children," British Journal of Surgery, Nov. 1958, vol. 46 (197), pp. 218-223.
Buss et al., "Direct Identification of Palmitic Acid as the Lipid Attached to p2lras," Molecular and Cellular Biology, Jan. 1986, vol. 6 (1), pp. 116-122.
Buss et al., "Myristic Acid Is Attached to the Transforming Protein of Rous Sarcoma Virus During or Immediately After Synthesis and Is Present in Both Soluble and Membrane-Bound Forms of the Protein," Molecular and Cellular Biology, Dec. 1984, vol. 4 (12), pp. 2697-2704.
Cabanillas, "Non-hodgkin's Lymphoma: the Old and the New," Clinical Lymphoma, Myeloma and Leukemia, Jun. 2011, vol. 11 (Suppl 1), pp. S87-S90.
Canadian Patent Application No. 2,842,443, Office Action dated May 9, 2018.
Canadian Cancer Society's Steering Committee on Cancer Statistics. Canadian Cancer Statistics 2011. Toronto, ON: Canadian Cancer Society, May 2011, 135 pages.
Carr et al., "N-tetradecanoyl Is the NH2-terminal Blocking Group of the Catalytic Subunit of Cyclic AMP-dependent Protein Kinase From Bovine Cardiac Muscle," Proceedings of the National Academy of Sciences of the United States of America, Oct. 1982, vol. 79 (20), pp. 6128-6131.
Charron et al., "Robust Fluorescent Detection of Protein Fatty-Acylation With Chemical Reporters," Journal of the American Chemical Society, Apr. 2009, vol. 131 (13), pp. 4967-4975.
Chen et al., "Regulation of G Proteins by Covalent Modification," Oncogene, Mar. 2001, vol. 20 (13), pp. 1643-1652.
Chen et al., "The Regulation of Autophagy—Unanswered Questions," Journal of Cell Science, Jan. 2011, vol. 124 (Pt 2), pp. 161-170.
Chinese Patent Application No. 201280046437.8, Office Action dated May 22, 2018—English Translation Not Available.
Chinese Patent Application No. 201280046437.8, First Office Action dated Feb. 28, 2015—English Translation available.
Chinese Patent Application No. 201280046437.8, Second Office Action dated Jan. 8, 2016—English Translation available.
Chinese Patent Application No. 201280046437.8, Third Office Action dated Sep. 9, 2016—English Translation available.
Chinese Patent Application No. 201380056950.X, Office Action dated Nov. 3, 2017—with unofficial English translation.
Chinese Patent Application No. CN 201380056950.X, Office Action dated May 5, 2016—English Translation available.
Chinese Patent Application No. CN 201380056950.X, Second Office Action dated Feb. 27, 2017—English Translation available.
Chinese Patent Application No. CN2012846437, Office Action dated Jun. 12, 2017—English Translation Available.
Choi et al., "N-Myristoylated c-Abl Tyrosine Kinase Localizes to the Endoplasmic Reticulum upon Binding to an 41losteric Inhibitor," The Journal of Biological Chemistry, Oct. 2009, vol. 284 (42), pp. 29005-29014.
Chou et al., "Quantitative Analysis of Dose-Effect Relationships: the Combined Effects of Multiple Drugs or Enzyme Inhibitors," Advances in Enzyme Regulation, 1984, vol. 22, pp. 27-55.
Cohen, "Caspases: The Executioners of Apoptosis," Biochemical Journal, Aug. 1997, vol. 326 (Pt 1), pp. 1-16.
Cordeddu et al., "Mutation of SHOC2 Promotes Aberrant Protein N-Myristoylation and Causes Noonan-Like Syndrome with Loose Anagen Hair," Nature Genetics, Sep. 2009, vol. 41 (9), pp. 1022-1026.

(56) References Cited

OTHER PUBLICATIONS

Cordo et al., "Myristic Acid Analogs are Inhibitors of Junin Virus Replication," Microbes and Infection, Jul. 1999, vol. 1 (8), pp. 609-614.
Cory et al., "Use of an Aqueous Soluble Tetrazolium/Formazan Assay for Cell Growth Assays in Culture," Cancer Communication, Jul. 1991, vol. 3 (7), pp. 207-212.
Crawford et al., "Conservation of Caspase Substrates Across Metazoans Suggests Hierarchical Importance of Signaling Pathways Over Specific Targets and Cleavage Site Motifs in Apoptosis," Cell Death & Differentiation, Dec. 2012, vol. 19 (12), pp. 2040-2048.
Cross et al., "A Short Sequence in the p60src N Terminus Is Required for p60src Myristylation and Membrane Association and for Cell Transformation," Molecular and Cellular Biology, Sep. 1984, vol. 4 {9), pp. 1834-1842.
Dang et al., "c-Myc Target Genes Involved in Cell Growth, Apoptosis, and Metabolism," Molecular and Cellular Biology, Jan. 1999, vol. 19 (1), pp. 1-11.
Dave et al., "Molecular Diagnosis of Burkitt's Lymphoma," The New England Journal of Medicine, Jun. 2006, vol. 354 {23), pp. 2431-2442.
Dawson et al., "Cancer Epigenetics: from Mechanism to Therapy," Cell, Jul. 2012, vol. 150 {1), pp. 12-27.
De La Puent A et al., Tris DBA Palladium Overcomes Hypoxia Mediated Drug Resistance in Multiple Myeloma. Leuk Lymphoma, Jul. 2016, vol. 57 (7), pp. 1677-1686.
Deichaite et al., "In Vitro Synthesis of pp60v-src: Myristylation in a Cell-Free System," Molecular and Cellular Biology, Oct. 1988, vol. 8 (10), pp. 4295-4301.
Dekker et al., "Small-Molecule Inhibition of APT1 Affects Ras Localization and Signaling," Nature Chemical Biology, Jun. 2010, vol. 6 (6), pp. 449-456.
Devadas et al., "Design and Synthesis of Novel Imidazole-Substituted Dipeptide Amides as Potent and Selective Inhibitors of Candida albicans MyristoylCoA:Protein N-Myristoyltransferase and Identification of Related Tripeptide Inhibitors with Mechanism-Based Antifungal Activity," Journal of Medicinal Chemistry, Aug. 1997, vol. 40 (16), pp. 2609-2625.
Devadas et al.L, "Substrate Specificity of *Saccharomyces cerevisiae* Myristoyi-CoA:Protein N-Myristoyltransferase. Analysis of Fatty Acid Analogs Containing Carbonyl Groups, Nitrogen Heteroatoms, and Nitrogen Heterocycles in an I Vitro Enzyme Assay and Subsequent Identification of Inhibitors of Human Immunodeficiency Virus I Replication," The Journal of Biological Chemistry, Apr. 1992, vol. 267 (11), pp. 7224-7239.
Disease Information. The Leukemia and Lymphoma Society, Search Disease Information. Accessed on Apr. 11, 2016 (1 page) [online]. Retrieved from the Internet:.
Dix et al., "Global Mapping of the Topography and Magnitude of Proteolytic Events in Biological Systems," Cell, Aug. 2008, vol. 134 (4), pp. 679-691.
Draper et al., "Palmitoyl Acyltransferase Assays and Inhibitors ," Molecular Membrane Biology, Jan. 2009, vol. 26 (1), pp. 5-13.
Ducker et al., "Two N-Myristoyltransferase Isozymes Play Unique Roles in Protein Myristoylation, Proliferation, and Apoptosis," Molecular Cancer Research, Aug. 2005, vol. 3 (8), pp. 463-476.
Duronio et al., "Disruption of the Yeast N-myristoyl Transferase Gene Causes Recessive Lethality," Science, Feb. 1989, vol. 243 (4892), pp. 796-800.
Duronio et al., "Mutations of Human Myristoyl-coa:protein N-Myristoyltransferase Cause Temperature-sensitive Myristic Acid Auxotrophy in Saccharomyces Cerevisiae," Proceedings of the National Academy of Sciences of the United States of America, May 1992, vol. 89 (9), pp. 4129-4133.
Dyda et al., "GCN5-Related N-Acetyltransferases: A Structural Overview," Annual Review of Biophysics and Biomolecular Structure, 2000, vol. 29, pp. 81-103.

Eisenhaber et al., "Prediction of Lipid Posttranslational Modifications and Localization Signals From Protein Sequences: Dig-pi, NMT and PTS1," Nucleic Acids Research, Jul. 2003, vol. 31 (13), pp. 3631-3634.
Enari et al., "A Caspase-Activated Dnase That Degrades DNA During Apoptosis, and Its Inhibitor ICAD," Nature, Jan. 1998, vol. 391 (6662), pp. 43-50.
European Patent Application No. 12817041.2, Office Action dated Dec. 20, 2017.
European Patent Application No. 12817041, Extended European Search Report dated Dec. 12, 2014.
European Patent Application No. 12817041, Supplementary European Search Report dated Feb. 26, 2015.
European Patent Application No. 13852049, Extended European Search Report dated Jun. 28, 2016.
European Patent Application No. 13852049, Partial European Search Report dated Feb. 25, 2016.
European Patent Application No. 13852049.9, Communication pursuant to Article 94(3) EPC dated Oct. 6, 2017.
Fadeel et al., "Apoptosis: a Basic Biological Phenomenon With Wide-Rnging Implications in Human Disease," Journal of Internal Medicine, Dec. 2005, vol. 258 (6), pp. 479-517.
Farazi et al., "The Biology and Enzymology of Protein N-Myristoylation," The Journal of Biological Chemistry, Oct. 2001, vol. 276 (43), pp. 39501-39504.
Farmer et al., "Targeting the Dna Repair Defect in Brca Mutant Cells as a Therapeutic Strategy," Nature, Apr. 2005, vol. 434 (7035), pp. 917-921.
FDA, Guidance for Industry and FDA Staff: Interpretation of the Term "Chemical Action" in the Definition of Device Under Section 201 (h) of the Federal Food, Drug, and Cosmetic Act. Accessed online at https://www.fda.gov/downloads/RegulatoryInformation/Guidances/UCM259068.pdf. Jun. 2011, 9 pages.
FDA, Information for Consumers (Biosimilars). Accessed online at https://www.fda.gov/Drugs/DevelopmentApprovaiProcess/HowDrugsareDevelopedandApproved/ApprovaiApplications/TherapeuticBiologicApplications/Biosimilars/ucm241718.html. page last updated Aug. 27, 2015, 5 pages.
Feinberg et al., "The History of Cancer Epigenetics," Nature Reviews Cancer, Feb. 2004, vol. 4 (2), pp. 143-153.
Felsted et al., "Protein N-Myristoylation as a Chemotherapeutic Target for Cancer," Journal of the National Cancer Institute, Nov. 1995, vol. 87 (211), pp. 1571-1573.
Ferrara et al., "Cost-effectiveness Analysis of the Addition of Rituximab to CHOP in Young Patients With Good-prognosis Diffuse Large-B-cell Lymphoma," Clinical Drug Investigation, 2008, vol. 28 (1), pp. 55-65.
Fong et al., "Inhibition of Poly(ADP-Ribose) Polymerase in Tumors From BRCA Mutation Carriers," The New England Journal of Medicine, Jul. 2009, vol. 361 (2), pp. 123-34.
Foon et al, "Novel Therapies for Aggressive B-cell Lymphoma," Advances in Hematology, 2012, vol. 2012, pp. 22.
Frearson et al., "N-Myristoyltransferase Inhibitors as New Leads to Treat Sleeping Sickness," Nature, Apr. 2010, vol. 464 (7289), pp. 728-732.
French et al., "Cyclohexyl-Octahydro-Pyrrolo[1,2-a]Pyrazine-Based Inhibitors of Human N-Myristoyltransferase-1," Journal of Pharmacology and Experimental Therapeutics, Apr. 2004, vol. 309 (1), pp. 340-347.
Frottin et al., "The Proteomics of N-terminal Methionine Cleavage," Molecular Cellular Proteomics, Dec. 2006, vol. 5 (12), pp. 2336-2349.
Fukata et al., "Protein Palmitoylation in Neuronal Development and Synaptic Plasticity," Nature Reviews Neuroscience, Mar. 2010, vol. 11 (3), pp. 161-175.
Gamper et al., "Gene Expression Profile of Blader Tissue of Patients with Ulcerative Interstitial Cystitis,"BMC Genomics, Apr. 28, 2009, vol. 10 (199), pp. 1-17.
Gatto et al., "The Germinal Center Reaction," The Journal of Allergy and Clinical Immunology, Nov. 2010, vol. 126 (5), pp. 898-907, quiz 908-9.

(56) References Cited

OTHER PUBLICATIONS

Giang et al., "A Second Mammalian N-Myristoyltransferase," The Journal of Biological Chemistry, Mar. 1998, vol. 273 (12), pp. 6595-6598.
Glover et al., "Human N-Myristoyltransferase Amino-terminal Domain Involved in Targeting the Enzyme to the Ribosomal Subcellular Fraction," The Journal of Biological Chemistry, Nov. 1997, vol. 272 (45), pp. 28680-28689.
Goncalves et al., "A Fluorescence-Based Assay for N-Myristoyltransferase Activity," Analytical Biochemistry, Feb. 2012, vol. 421 (1), pp. 342-344.
Greaves et al., "DHHC Palmitoyl Transferases: Substrate Interactions and (Patho) Physiology," Trends in Biochemical Sciences, May 2011, vol. 36 (5), pp. 245-253.
Griffin et al., "A Study of Rituximab and Ifosfamide, Carboplatin, and Etoposide Chemotherapy in Children with Recurrent/Refractory B-cell (CD20+) Non-Hodgkin Lymphoma and Mature B-Cell Acute Lymphoblastic Leukemia: A Report from the Children's Oncology Group," Pediatric Blood & Cancer, Feb. 2009, vol. 52 (2), pp. 177-181.
Gsselbrecht et al., "Salvage Regimens with Autologous Transplantation for Relapsed Large B-Cell Lymphoma in : he Rituximab Era," Journal of Clinical Oncology, Sep. 2010, vol. 28 (27), pp. 4184-4190.
Gui et al., "Histone Deacetylase (HDAC) Inhibitor Activation of p21WAF1 Involves Changes in Promoter Associated Proteins, Including HDAC1," Proceedings of the National Academy of Sciences of the United States of America, Feb. 2004, vol. 101 (5), pp. 1241-1246.
Gutkowska et al., "Structure, Regulation and Cellular Functions of Rab Geranylgeranyl Transferase and Is Cellular Partner Rab Escort Protein," Molecular Membrane Biology, Nov. 2012, vol. 29 (7), pp. 243-256.
Hancock et al., "All Ras Proteins are Polyisoprenylated but Only Some are Palmitoylated," Cell, Jun. 1989, vol. 57 (7), pp. 1167-1177.
Hang et al., "Chemical probes for the rapid detection of Fatty-acylated proteins in Mammalian cells.," Journal of the American Chemical Society, Mar. 2007, vol. 129 (10), pp. 2744-2745.
Hang et al., "Exploring Protein Lipidation With Chemical Biology," Chemical Reviews, Oct. 2011, vol. 111 (10), pp. 6341-6358.
Hannoush et al., "Imaging the Lipidome: omega-Alkynyl Fatty Acids for Detection and Cellular Visualization of Lipid-Modified Proteins," ACS Chemical Biology, Jul. 2009, vol. 4 (7), pp. 581-587.
Hannoush et al., "The Chemical Toolbox for Monitoring Protein Fatty Acylation and Prenylation," Nature Chemical Biology, Jul. 2010, vol. 6 (7), pp. 498-506.
Hantschel et al., "A Myristoyl/Phosphotyrosine Switch Regulates c-Abl," Cell, Mar. 2003, vol. 112 (6), pp. 845-857.
Harper et al., "Inhibition of Varicella-Zoster Virus Replication by an Inhibitor of Protein Myristoylation," The Journal of General Virology, Jun. 1993, vol. 74 (Pt 6), pp. 1181-1184.
Heal et al., "Bioorthogonal Chemical Tagging of Protein Cholesterylation in Living Cells," Chemical Communications, Apr. 2011, vol. 47 (14), pp. 4081-4083.
Hedo et al., "Myristyl and Palmityl Acylation of the Insulin Receptor," The Journal of Biological Chemistry, Jan. 1987, vol. 262 (3), pp. 954-957.
Hirsch et al., "Easily Reversible Desthiobiotin Binding to Streptavidin, Avidin, and Other Biotin-binding Proteins: Uses for Protein Labeling, Detection, and Isolation," Analytical Biochemistry, Sep. 2002, vol. 308 (2), pp. 343-357.
Hobeika et al., "Testing Gene Function Early in the B Cell Lineage in Mb1-cre Mice.," Proceedings of the National Academy of Sciences of the United States of America, Sep. 2006, vol. 103 (37), pp. 13789-13794.

Hu et al., "Myristoylated Naked2 Antagonizes Wnt-beta-catenin Activity by Degrading Dishevelled-1 at the Plasma Membrane," The Journal of Biological Chemistry, Apr. 2010, vol. 285 (18), pp. 13561-13568.
Hudson et al., "Sect 2.4: Viable Lymphocyte Count," found in Practical Immunology, Blackwell Scientific Publications, Oxford, England, 1976, 29-32.
Hummel et al., "A Biologic Definition of Burkitt's Lymphoma From Transcriptional and Genomic Profiling," The New England Journal of Medicine, Jun. 2006, vol. 354 (23), pp. 2419-2430.
Inoue et al., "Ordering of Caspases in Cells Undergoing Apoptosis by the Intrinsic Pathway," Cell Death and Differentiation, 2009, vol. 16 (7), pp. 1053-1061.
International Patent Application No. PCT/CA2012/000696, International Preliminary Report on Patentability dated Feb. 6, 2014.
International Patent Application No. PCT/CA2012/000696, International Search Report dated Nov. 7, 2012.
International Patent Application No. PCT/CA2013/050821, International Preliminary Report on Patentability dated May 14, 2015.
International Patent Application No. PCT/CA2013/050821, International Search Report dated Feb. 5, 2014.
Israel Patent Application No. 230575, Office Action dated May 23, 2018—English Translation available.
Israel Patent Application No. IL230575, Office Action dated Dec. 11, 2016—English Translation available.
Israeli Patent Application No. 238481, Office Action dated Nov. 6, 2017—English Translation available.
Iversen et al., "Cell Kinetics of African Cases of Burkitt Lymphoma. A Preliminary Report," European Journal of Cancer, Jun. 1972, vol. 8 (3), pp. 305-308.
Jackson et al., "N-Terminal Mutations Activate the Leukemogenic Potential of the Myristoylated form of c-abl," The EMBO Journal, Feb. 1989, vol. 8 (2), pp. 449-456.
Jaffe, "The 2008 WHO Classification of Lymphomas: Implications for Clinical Practice and Translational Research," Hematology-American Society of Hematology Education Program, 2009, pp. 523-531.
Jakobi., "Subcellular Targeting Regulates the Function of Caspase-Activated Protein Kinases in Apoptosis," Drug Resistance Updates, Feb. 2004, vol. 7 (1), pp. 11-17.
Japanese Patent Application No. 2014-520475, Notice of Allowance dated Dec. 4, 2017—English Translation Available.
Japanese Patent Application No. 2014-520475, Office Action dated Apr. 10, 2017—English Translation available.
Japanese Patent Application No. 2014-520475, Office Action dated May 9, 2016—English Translation available.
Japanese Patent Application No. 2015-0538225, Office Action dated Jul. 10, 2017—with English Translation.
Japanese Patent Application No. 2015-0538225, Office Action dated May 21, 2018—English Translation Available.
Juo et al., "Essential Requirement for Caspase-8/FLICE in the Initiation of the Fas-Induced Apoptotic Cascade," Current Biology, Sep. 1998, vol. 8 (18), pp. 1001-1008.
Kaelin., "The Concept of Synthetic Lethality in the Context of Anticancer Therapy," Nature Reviews Cancer, Sep. 2005, vol. 5 (9), pp. 689-698.
Kagawa et al., "Deficiency of Caspase-3 in MCF7 Cells Blocks Bax-mediated Nuclear Fragmentation but not Cell Death," Clinical Cancer Research, May 2001, vol. 7 (5), pp. 1474-1480.
Kamps et al., "Mutation of NH2-Terminal Glycine of p60src Prevents Both Myristoylation and Morphological Transformation," Proceedings of the National Academy of Sciences, Jul. 1985, vol. 82 (14), pp. 4625-4628.
Kasahara et al., "Rapid Trafficking of C-Src, a Non-Palmitoylated Src-Family Kinase, Between the Plasma Membrane and Late Endosomes/Lysosomes," Experimental Cell Research, Jul. 2007, vol. 313 (12), pp. 2651-2666.
Kay et al., "Tris (Dibenzylideneacetone) Dipalladium a Small-Molecule Palladium Complex Is Effective in the Induction of Apoptosis for B-Chronic Lymphocytic Leukemia B-Cells," Blood, 2011, vol. 118, pp. 2851.

(56) References Cited

OTHER PUBLICATIONS

Kelly et al., "Burkitt Lymphoma: Revisiting the Pathogenesis of a Virus-Associated Malignancy," Hematology American Society of Hematology Education Program, 2007, vol. 1, pp. 277-284.

Kenkre et al., "Burkitt Lymphoma/Leukemia: Improving Prognosis," Clinical Lymphoma, Myeloma & Leukemia Supplement, 2009, vol. 9 Suppl 3, pp. 3231-3238.

Kim et al., "Src Kinases as Therapeutic Targets for Cancer," Nature Reviews Clinical Oncology, Oct. 2009, vol. 6 (10), pp. 587-595.

King et al., "Demonstration of Multiple Forms of Bovine Brain Myristoyl Coa:Protein N-Myristoyl Transferase," Molecular and Cellular Biochemistry, Jul. 1992, vol. 113 (1), pp. 77-81.

King et al., "Identification, Purification and Characterization of a Membrane-Associated N-Myristoyltransferase Inhibitor Protein from Bovine Brain," Biochemical Journal, Apr. 1993, vol. 291 (Pt 2), pp. 635-639.

King et al., "N-Myristoyl Transferase Assay Using Phosphocellulose Paper Binding," Analytical Biochemistry, Dec. 1991, vol. 199 (2), pp. 149-153.

Kishore et al., "The Substrate Specificity of *Saccharomyces cereuisiae* Myristoyl-CoA: Protein N-Myristoyltransferase. Analysis of Myristic Acid Analogs Containing Oxygen, Sulfur, Double Bonds, Triple Bonds, and/or an Aromatic Residue," The Journal of Biological Chemistry, May 1991, vol. 266 (14), pp. 8835-8855.

Kojima et al., "Ghrelin is a Growth-Hormone-Releasing Acylated Peptide from Stomach," Nature, Dec. 1999, vol. 402 (6762), pp. 656-660.

Kon et al., "Chaperone-Mediated Autophagy in Health and Disease," FEBS Letters, Apr. 2010, vol. 584 (7), pp. 1399-1404.

Korycka et al., "Human DHHC Proteins: A Spotlight on the Hidden Player of Palmitoylation," The European Journal of Cell Biology, Feb. 2012, vol. 91 (2), pp. 107-117.

Kostiuk et al., "Identification of Palmitoylated Mitochondrial Proteins Using a Bio-orthogonal Azido-palmitate Analogue," FASEB Journal, Mar. 2008, vol. 22 (3), pp. 721-732.

Kovalchuk et al., "Burkitt Lymphoma in the Mouse," The Journal of Experimental Medicine, Oct. 2000, vol. 192 (8), pp. 1183-1190.

Kumar et al., "The Potential Use of N-Myristoyltransferase as a Biomarker in the Early Diagnosis of Colon Cancer," Cancers (Basel), Mar. 2011, vol. 3 (1), pp. 1372-1382.

Kuppers, "Mechanisms of B-cell Lymphoma Pathogenesis," Nature Reviews Cancer, Apr. 2005, vol. 5 (4), pp. 251-262.

Laemmli, "Cleavage of Structural Proteins During the Assembly of the Head of Bacteriophage T4," Nature, Aug. 1970, vol. 227 (5259), pp. 680-685.

Leatherbarrow, "Grafit User's Guide (Version 6)," Erithacus Software Ltd., Horley, United Kingdom. 2009, pp. 1-294.

Lee , "A Capacitance-Based Method for Experimental Determination of Metallurgical Channel Length of Submicron LDD MOSFET's," IEEE Transactions on Electron Devices, Mar. 1994, vol. 41 (3), pp. 403-412.

Lee et al., "Costs Associated with Diffuse Large B-Cell Lymphoma Patient Treatment in a Canadian Integrated Cancer are Center ," Value Health , Mar.-Apr. 2008 , vol. 11 (2) , pp. 221-230.

Lee et al., "Prognosis of Chronic Lymphocytic Leukemia: a Multivariate Regression Analysis of 325 Untreated Patients," Blood, Mar. 1987, vol. 69 (3), pp. 929-936.

Lenz et al., "Aggressive Lymphomas," The New England Journal of Medicine, Apr. 2010, vol. 362 (15), pp. 1417-1429.

Leuenroth et al., "The Loss of Mcl-1 Expression in Human Polymorphonuclear Leukocytes Promotes Apoptosis," Journal of Leukocyte Biology, Jul. 2000, vol. 68 (1), pp. 158-166.

Liang et al., "Mass Spectrometric Analysis of GAP-43/neuromodulin Reveals the Presence of a Variety of Fatty Acylated Species," The Journal of Biological Chemistry, Sep. 2002, vol. 277 (36), pp. 33032-33040.

Liang et al., "The N-Terminal SH4 Region of the Src Family Kinase Fyn Is Modified by Methylation and Heterogeneous Fatty Acylation: Role in Membrane Targeting, Cell Adhesion, and Spreading," The Journal of Biological Chemistry, Feb. 2004, vol. 279 (9), pp. 8133-8139.

Lim et al, (Abstract) P004:Understanding the roles of NMT1 and NMT2 cancers. Accessed online at https://www.biochemistry.org/Portals/0/Conferences/Abstracts/SA164/SA164P004.pdf on Mar. 10, 2017, 1 page.

Lin et al., "Protein Lysine Acylation and Cysteine Succination by Intermediates of Energy Metabolism," ACS Chemical Biology, Jun. 2012, vol. 7 (6), pp. 947-960.

Liston et al., "The Inhibitors of Apoptosis: There is More to Life Than Bcl2," Oncogene, Nov. 2003, vol. 22 (53), pp. 8568-8580.

Liu et al., "Targeting the Protein Prenyltransferases Efficiently Reduces Tumor Development in Mice With K-RAS-Induced Lung Cancer," Proceedings of the National Academy of Sciences of the United States of America, Apr. 2010, vol. 107 (14), pp. 6471-6476.

Lobo et al., "Identification of a Ras Palmitoyltransferase in Saccharomyces Cerevisiae," The Journal of Biological Chemistry, Oct. 2002, vol. 277 (43), pp. 41268-41273.

Lodge et al., "Comparison of Myristoyl-CoAProtein N-Myristoyltransferases from Three Pathogenic Fungi: Cryptococcus Neoformans," The Journal of Biological Chemistry, Jan. 1994, vol. 269 (4), pp. 2996-3009.

Lodge et al., "Targeted Gene Replacement Demonstrates That Myristoyl-CoA: Protein N-myristoyltransferase is Essential for Viability of Cryptococcus Neoformans," Proceedings of the National Academy of Sciences of the United States of America, Dec. 1994, vol. 91 (25), pp. 12008-12012.

Love et al., "The Genetic Landscape of Mutations in Burkitt Lymphoma," Nature Genetics, Dec. 2012, vol. 44 (12), pp. 1321-1325.

Lu et al., "Expression of N-myristoyltransferase in Human Brain Tumors," Neurochemical Research, Jan. 2005, vol. 30 (1), pp. 9-13.

Luciano et al., "Phosphorylation of Bim-el by Erk1/2 on Serine 69 Promotes Its Degradation via the Proteasome Pathway and Regulates Its Proapoptotic Function," Oncogene, Oct. 2003, vol. 22 (43), pp. 6785-6793.

Magee et al., "Fatty Acylation and Prenylation of Proteins: What's Hot in Fat," Current Opinion in Cell Biology, Apr. 2005, vol. 17 (2), pp. 190-196.

Magnuson et al., "Increased N-Myristoyltransferase Activity Observed in Rat and Human Colonic Tumors," Journal of the National Cancer Institute, Nov. 1995, vol. 87 (21), pp. 1630-1635.

Mahrus et al., "Global Sequencing of Proteolytic Cleavage Sites in Apoptosis by Specific Labeling of Protein N Termini," Cell, Sep. 2008, vol. 134 (5), pp. 866-876.

Mann et al., "Novel Lipid Modifications of Secreted Protein Signals," Annual Review of Biochemistry, 2004, vol. 73, pp. 891-923.

Martin et al., "Large-Scale Profiling of Protein Palmitoylation in Mammalian Cells," Nature Methods, Feb. 2009, vol. 6 (2), pp. 135-138.

Martin et al., "Post-Translational Myristoylation: Fat Matters in Cellular Life and Death," Biochimie, Jan. 2011, vol. 93 (1), pp. 18-31.

Martin et al., "Rapid Detection, Discovery, and Identification of Post-translationally Myristoylated Proteins During Apoptosis Using a Bio-orthogonal Azidomyristate Analog," FASEB Journal, Mar. 2008, vol. 22 (3), pp. 797-806.

Martin et al., "Tandem Reporter Assay for Myristoylated Proteins Post-translationally (TRAMPP) Identifies Novel Substrates for Post-Translational Myristoylation: PKCK, a Case Study," FASEB Journal, Jan. 2012, vol. 26 (1), pp. 13-28.

Massadi et al., "Ghrelin Acylation and Metabolic Control," Peptides, Nov. 2011, vol. 32 (11), pp. 2301-2308.

Matheson et al., "The Conservation of Amino Acids in the N-Terminal Position of Ribosomal and Cytosol Proteins from *Escherichia coli*, Bacillus Stearothermophilus, and Halobacterium Cutirubrum," Canadian Journal of Biochemistry, Dec. 1975, vol. 53 (12), pp. 1323-1327.

Maurer-Stroh et al., "N-Terminal N-Myristoylation of Proteins: Prediction of Substrate Proteins from Amino Acid Sequence," Journal of Molecular Biology, Apr. 2002, vol. 317 (4), pp. 541-557.

(56) References Cited

OTHER PUBLICATIONS

Maurer-Stroh et al., "N-Terminal N-Myristoylation of Proteins: Refinement of the Sequence Motif and its Taxon-Specific Differences," Journal of Molecular Biology, Apr. 2002, vol. 317 (4), pp. 523-540.
Maurer-Stroh et al., "Refinement and Prediction of Protein Prenylation Motifs," Genome Biology, 2005, vol. 6 (6), pp. R55.
Mayor et al., "Sorting GPI-Anchored Proteins," Sorting GPI-Anchored Proteins, Feb. 2004, vol. 5 (2), pp. 110-120.
McCabe et al., "Functional Roles for Fatty Acylated Aminoterminal Domains in Subcellular Localization," Molecular Biology of the Cell, Nov. 1999, vol. 10 (11), pp. 3771-3786.
McCabe et al., "N-Terminal Protein Acylation Confers Localization to Cholesterol, Sphingolipid-enriched Vlembranes But Not to Lipid Raffs/Caveolae," Molecular Biology of the Cell, Nov. 2001, vol. 12 (11), pp. 3601-3617.
McIlhinney et al., "Characterization and Cellular Localization of Human Myristoyl-Coa: Protein N-Myristoyltransferase," Biochemical Society Transactions, Aug. 1995, vol. 23 (3), pp. 549-553.
McIlhinney et al., "Immunocytochemical Characterization and Subcellular Localization of Human Vlyristoyl-CoA: Protein N-Myristoyltransferase in HeLa Cells.," Experimental Cell Research, Mar. 1996, vol. 223 (2), pp. 348-356.
McIlhinney et al., "Purification and Partial Sequencing of Myristoyl-CoA: Protein N-Myristoyltransferase from Bovine Drain," Biochemical Journal, Mar. 1993, vol. 290 (Pt 2), pp. 405-410.
McLaughlin et al., "The Myristoyl-Electrostatic Switch: A Modulator of Reversible Protein-Membrane Nteractions," Trends in Biochemical Sciences, Jul. 1995, vol. 20 (7), pp. 272-276.
McTaggart, "Isoprenylated Proteins," Cellular and Molecular Life Sciences, Feb. 2006, vol. 63 (3), pp. 255-267.
Merck Manual, 18th Edition, Japanese Edition, Nikkei BP, Apr. 25, 2007, pp. 1177-1186—English Translation available.
Mexican Patent Application No. MX/a/2014/000661, Office Action dated Aug. 7, 2018—English Translation Not Available.
Mexican Patent Application No. 20140000661, Office Action dated Mar. 8, 2017.
Mexican Patent Application No. MX/a/2014/000661, Office Action dated Nov. 6, 2017—With Unofficial English Translation.
Miles et al., "Risk Factors and Treatment of Childhood and Adolescent Burkitt Lymphoma/Leukaemia," British Journal of Haematology, Mar. 2012, vol. 156 (6), pp. 730-743.
Mishkind, "Morbid Myristoylation," Trends in Cell Biology, May 2001, vol. 11 (5), pp. 191.
Mitchell et al., "Protein Palmitoylation by a Family of Dhhc Protein S-Acyltransferases," Journal of Lipid Research, Jun. 2006, vol. 47 (6), pp. 1118-1127.
Moffitt et al., "From Sentencing to Execution—The Processes of Apoptosis," The Journal of Pharmacy and Pharmacology, May 2010, vol. 62 (5), pp. 547-562.
Molyneux et al., "Burkitt's Lymphoma," Lancet (London, England), Mar. 2012, vol. 379 (9822), pp. 1234-1244.
Morgan et al., "Modulation of Anthracycline-Induced Cytotoxicity by Targeting the Prenylated Proteome in Myeloid Eukemia Cells," Journal of Molecular Medicine (Berlin, Germany), Feb. 2012, vol. 90 (2), pp. 149-161.
Nagata, "Apoptotic DNA Fragmentation," Experimental Cell Research, Apr. 2000, vol. 256 (1), pp. 12-18.
New Zealand Patent Application No. 707090, Examination Report dated Mar. 20, 2018.
New Zealand Patent Application No. 737605, Examination Report dated Apr. 12, 2018.
New Zealand Patent Application No. 620167, First Examination Report dated Nov. 24, 2014.
New Zealand Patent Application No. 720441, First Examination Report dated May 25, 2016.
Nimchuk et al., "Eukaryotic Fatty Acylation Drives Plasma Membrane Targeting and Enhances Function of Several Type Iii Effector Proteins From Pseudomonas Syringae," Cell, May 2000, vol. 101 (4), pp. 353-363.
Novelli et al., "Protein Farnesylation and Disease," Journal of Inherited Metabolic Disease, Sep. 2012, vol. 35 (5), pp. 917-926.
Ntwasa et al., "Drosophila Embryos Lacking N-myristoyltransferase Have Multiple Developmental Defects," Experimental Cell Research, Jan. 2001, vol. 262 (2), pp. 134-144.
Ntwasa et al., "Sequence and Expression of Drosophila Myristoyl-CoA: Protein N-Myristoyl Transferase: Evidence or Proteolytic Processing and Membrane Localisation," Journal of Cell Science, Jan. 1997, vol. 110 (Pt 2), pp. 149-156.
Ohno et al., "Intracellular Localization and Tissue-Specific Distribution of Human and Yeast DHHC Cysteine-Rich Domain-Containing Proteins," Biochimica et Biophysica Acta, Apr. 2006, vol. 1761 (4), pp. 474-483.
Olsson et al., "Caspases and Cancer," Cell Death and Differentiation, Sep. 2011, vol. 18 (9), pp. 1441-1449.
Paige et al., "Metabolic Activation of 2-Substituted Derivatives of Myristic Acid to Form Potent Inhibitors of Myristoyl CoA:Protein N-Myristoyltransferase," Biochemistry, Nov. 1990, vol. 29 (46), pp. 10566-10573.
Panethymitaki et al., "Characterization and Selective Inhibition of Myristoyl-CoA:protein N-myristoyltransferase From Trypanosoma Brucei and Leishmania Major," The Biochemical Journal, Jun. 2006, vol. 396 (2), pp. 277-285.
Parekh et al, "Therapeutic Targeting of the BCL6 Oncogene for Diffuse Large B-cell Lymphomas," Leukemia and Lymphoma, May 2008, vol. 49 (5), pp. 874-882.
Patwardhan et al., "Myristoylation and Membrane Binding Regulate c-Src Stability and Kinase Activity," Molecular and Cellular Biology, Sep. 2010, vol. 30 (17), pp. 4094-4107.
Paulick et al., "The Glycosylphosphatidylinositol Anchor: A Complex Membrane-Anchoring Structure for Proteins," Biochemistry, Jul. 2008, vol. 47 (27), pp. 6991-7000.
Pegram et al., "Rational Combinations of Trastuzumab With Chemotherapeutic Drugs Used in the Treatment of Breast Cancer," Journal of the National Cancer Institute, May 2004, vol. 96 (10), pp. 739-749.
Peitzsch et al., "Binding of Acylated Peptides and Fatty Acids to Phospholipid Vesicles: Pertinence to Vlyristoylated Proteins," Biochemistry, Oct. 1993, vol. 32 (39), pp. 10436-10443.
Perinpanayagam et al., "Regulation of Co- And Post-Translational Myristoylation of Proteins During Apoptosis: Nterplay of N-Myristoyltransferases and Caspases," The FASEB Journal, Feb. 2013, vol. 27 (2), pp. 811-821.
Perkins et al., "Burkitt Lymphoma in Adults," Hematology American Society of Hematology Education Program, 2008, pp. 341-348.
Peseckis et al., "Fatty Acyl Transfer by Human N-Myristyl Transferase Is Dependent Upon Conserved Cysteine and Histidine Residues," The Journal of Biological Chemistry, Dec. 1994, vol. 269 (49), pp. 30888-30892.
Peseckis et al., "Iodinated Fatty Acids as Probes for Myristate Processing and Function. Incorporation into pp60v-src.1," The Journal of Biological Chemistry, Mar. 1993, vol. 268 (7), pp. 5107-5114.
Phan et al., "The BCL6 Proto-Oncogene Suppresses P53 Expression in Germinal-Centre B Cells," Nature, Dec. 2004, vol. 432 (7017), pp. 635-639.
Podell, "Predicting N-Terminal Myristoylation Sites in Plant Proteins," BMC Genomics. Jun. 2004, 17 (51): 37.
Porter et al., "Cholesterol Modification of Hedgehog Signaling Proteins in Animal Development," Science, Oct. 1996, vol. 274 (5285), pp. 255-259.
Prasad et al., "N-Myristoyltransferase: A Novel Target," Mini-Reviews in Medicinal Chemistry, Feb. 2008, vol. 8 (2), pp. 142-149.
Price et al., "Myristoyl-CoA:Protein N-Myristoyltransferase, an Essential Enzyme and Potential Drug Target in Kinetoplastid Parasites," The Journal of Biological Chemistry, Feb. 2003, vol. 278 (9), pp. 7206-7214.
Puente et al.,"Tris DBA Palladium Overcomes Hypoxia Mediated Drug Resistance in Multiple Myeloma," Journal of Blood, 2015, p. 2978.
Rajala et al., "Increased Expression of N-Myristoyltransferase in Gallbladder Carcinomas," Cancer, May 2000, vol. 88 (9), pp. 1992-1999.

(56) References Cited

OTHER PUBLICATIONS

Raju et al., "Molecular Cloning and Biochemical Characterization of Bovine Spleen Myristoyl CoA:Protein N-Vlyristoyltransferase," Archives Biochemistry Biophysics, Dec. 1997, vol. 348 (1), pp. 134-142.
Raju et al., "N-Myristoyltransferase Overexpression in Human Colorectal Adenocarcinomas," Experimental Cell Research, Aug. 1997, vol. 235 (1), pp. 145-154.
Raju et al., "Preparation and Assay of Myristoyl-CoA:Protein N-Myristoyltransferase," Methods in Molecular Biology, 1999, vol. 116, pp. 193-211.
Rasti et al., "Circulating Epstein-Barr Virus in Children Living in Malaria-Endemic Areas," Scandinavian Journal of Immunology, May 2005, vol. 61 (5), pp. 461-465.
Resh, "Fatty Acylation of Proteins: New Insights into Membrane Targeting of Myristoylated and Palmitoylated Proteins," Biochimica et Biophysica Acta, Aug. 1999, vol. 1451 (1), pp. 1-16.
Resh, "Myristylation and Palmitylation of Src Family Members: The Fats of the Matter," Cell, Feb. 1994, vol. 76 (3), pp. 411-413.
Resh, "Palmitoylation of Ligands, Receptors, and Intracellular Signaling Molecules," Science's STKE : Signal Transduction Knowledge Environment, Oct. 2006, vol. 2006 (359), pp. re14.
Resh, "Trafficking and Signaling by Fatty-Acylated and Prenylated Proteins," Nature Chemical Biology, Nov. 2006, vol. 2 (11), pp. 584-590.
Richter-Larrea et al., "Reversion of Epigenetically Mediated BIM Silencing Overcomes Chemoresistance in Burkitt Ymphoma," Blood, Oct. 2010, vol. 116 (14), pp. 2531-2542.
Rioux et al., "Identification and Characterization of Recombinant and Native Rat Myristoyl-coa: Protein N-Mlyristoyltransferases," Molecular and Cellular Biochemistry, Jun. 2006, vol. 286 (1-2), pp. 161-170.
Rocks et al., "An Acylation Cycle Regulates Localization and Activity of Palmitoylated Ras Isoforms," Science, Mar. 2005, vol. 307 (5716), pp. 1746-1752.
Rocque et al., "A Comparative Analysis of the Kinetic Mechanism and Peptide Substrate Specificity of Human and *Saccharomyces cerevisiae* Myristoyl-CoA:Protein N-Myristoyltransferase," The Journal of Biological Chemistry, May 1993, vol. 268 (14), pp. 9964-9971.
Roskoski, "Protein Prenylation: A Pivotal Posttranslational Process," Biochemical and Biophysical Research Communications, Mar. 2003, vol. 303 (1), pp. 1-7.
Rostovtsev et al., "A Stepwise Huisgen Cycloaddition Process: Copper(I)-Catalyzed Regioselective Ligation of Azides and Terminal Alkynes," Angewandte Chemie (International ed. in English), Jul. 2002, vol. 41 (14), pp. 2596-2599.
Rouleau et al., "PARP Inhibition: PARP1 and Beyond," Nature Reviews Cancer, Apr. 2010, vol. 10 (4), pp. 293-301.
Rudel et al., "Membrane and Morphological Changes in Apoptotic Cells Regulated by Caspase-mediated Activation of PAK2," Science, 1997, vol. 276 (5318), pp. 1571-1574.
Rudnick et al., "Analogs of Palmitoyl-CoA That Are Substrates for Myristoyl-coa:protein N-Myristoyltransferase," Proceedings of the National Academy of Sciences of the United States of America, Nov. 1992, vol. 89 (21), pp. 10507-10511.
Rudnick et al., "Kinetic and Structural Evidence for a Sequential Ordered Bi Bi Mechanism of Catalysis by *Saccharomyces cerevisiae* Myristoyl-CoA: Protein N-Myristoyltransferase," The Journal of Biological Chemistry, May 1991, vol. 266 (15), pp. 9732-9739.
Rudnick et al., "Studies of the Catalytic Activities and Substrate Specificities of *Saccharomyces cerevisiae* Myristoyl-menzyme A:Protein N-Myristoyltransferase Deletion Mutants and Human/Yeast Nmt Chimeras in *Escherichia coli* and *S. cerevisiae*," The Journal of Biological Chemistry, Nov. 1992, vol. 267 (33), pp. 23852-23861.
Russian Patent Application No. 2014101787, Office Action dated Jun. 27, 2018—English Translation Available.
Russian Patent Application No. 2014101787, Office Action dated Apr. 28, 2016—English Translation available.
Russian Patent Application No. 2014101787, Office Action dated Aug. 30, 2016—English Translation available.
Russian Patent Application No. 2014101787, Office Action dated Dec. 21, 2017—English Translation Available.
Russian Patent Application No. RU2015118294, Office Action dated Jul. 7, 2017 with English Translation.
Ryan et al., "Hedgehog Secretion and Signal Transduction in Vertebrates," The Journal of Biological Chemistry, May 2012, vol. 287 (22), pp. 17905-17913.
Saini et al., "Rituximab in Hodgkin Lymphoma: Is the Target Always a Hit?," Cancer Treatment Reviews, Aug. 2011, vol. 37 (5), pp. 385-390.
Sakurai et al., "Posttranslational N-myristoylation Is Required for the Anti-apoptotic Activity of Human Tgelsolin, the C-terminal Caspase Cleavage Product of Human Gelsolin," The Journal of Biological Chemistry, May 2006, vol. 281 (20), pp. 14288-14295.
Sato et al., "Differential Trafficking of Src, Lyn, Yes and Fyn Is Specified by the State of Palmitoylation in the SH4 Domain," Journal of cell science, Apr. 2009, vol. 122 (Pt 7), pp. 965-975.
Schey et al., "Novel Fatty Acid Acylation of Lens Integral Membrane Protein Aquaporin-0," Biochemistry, 2010, vol. 49 (45), pp. 9858-9865.
Schmidt-Supprian et al., "Excision of the Frt-flanked Neor Cassette From the CD19cre Knock-in Transgene Reduces 2, Re-Mediated Recombination," Transgenic Research, Oct. 2007, vol. 16 (5), pp. 657-660.
Seaton et al., "N-Myristoyltransferase Isozymes Exhibit Differential Specificity for Human Immunodeficiency Virus Type 1 Gag and Nef," The Journal of General Virology, Jan. 2008, vol. 89 (Pt 1), pp. 288-296.
Seer Cancer Statistics Review 1975-2010, [online]. , 86 pages.
Sehn et al., "Treatment of Aggressive Non-hodgkin's Lymphoma: A North American Perspective," Oncology, Apr. 2005, vol. 19 (4 Suppl 1), pp. 26-34.
Selvakumar et al., "N-myristoyltransferase 2 Expression in Human Colon Cancer: Cross-Talk Between the Calpain and Caspase System," FEBS Letters, Apr. 2006, vol. 580 (8), pp. 2021-2026.
Selvakumar et al., "Potential Role of N-Myristoyltransferase in Cancer," Progress in Lipid Research, Jan. 2007, vol. 46 (1), pp. 1-36.
Shawgo et al., "Caspase-9 Activation by the Apoptosome Is Not Required for Fas-mediated Apoptosis in Type II Jurkat Cells," The Journal of Biological Chemistry, Nov. 2009, vol. 284 (48), pp. 33447-33455.
Sheng et al., "Homology Modeling and Molecular Dynamics Simulation of N-Myristoyltransferase From Protozoan Parasites: Active Site Characterization and Insights Into Rational Inhibitor Design," Journal of Computer-Aided Molecular Design, Jun. 2009, vol. 23 (6), pp. 375-389.
Shrivastav et al., "Overexpression of Akt/PKB Modulates N-myristoyltransferase Activity in Cancer Cells," The Journal of Pathology, Jul. 2009, vol. 218 (3), pp. 391-398.
Shrivastav et al., "Potent Inhibitor of N-myristoylation: a Novel Molecular Target for Cancer," Cancer Research, Nov. 2003, vol. 63 (22), pp. 7975-7978.
Shrivastav et al., "Regulation of N-Myristoyltransferase by Novel Inhibitor Proteins," Cell Biochemistry and Biophysics, 2005, vol. 43 (1), pp. 189-202.
Sigal et al., "Amino-terminal Basic Residues of Src Mediate Membrane Binding Through Electrostatic Interaction With Acidic Phospholipids," Proceedings of the National Academy of Sciences of the United States of America, Dec. 1994, vol. 91 (25), pp. 12253-12257.
Sikorski et al., "Selective Peptidic and Peptidomimetic Inhibitors of Candida albicans MyristoylCoA: Protein N-Mlyristoyltransferase: A New Approach to Antifungal Therapy," Biopolymers, 1997, vol. 43 (1), pp. 43-71.
Silverman et al., "Lysine Residues Form an Integral Component of a Novel NH2-Terminal Membrane Targeting Motif for Myristylated pp60v-src," The Journal of Cell Biology, Oct. 1992, vol. 119 (2), pp. 415-425.
Singh et al., "Autophagy Regulates Lipid Metabolism," Nature, Apr. 2009, vol. 458 (7242), pp. 1131-1135.

(56) References Cited

OTHER PUBLICATIONS

Sjogren et al., "Inactivating GGTase-I Reduces Disease Phenotypes in a Mouse Model of K-RAS-Induced Myeloproliferative Disease," Leukemia, Jan. 2011, vol. 25 (1), pp. 186-189.
Smotrys et al., "Palmitoylation of Intracellular Signaling Proteins: Regulation and Function," Annual Review of Biochemistry, 2004, vol. 73, pp. 559-587.
Solary et al., "Proteases, Proteolysis, and Apoptosis," Cell Biology and Toxicology, Mar. 1998, vol. 14 (2), pp. 121-132.
Sperandio et al., "An Alternative, Nonapoptotic form of Programmed Cell Death," Proceedings of the National Academy of Sciences of the United States of America, Dec. 2000, vol. 97 (26), pp. 14376-14381.
Stevenson et al., "Myristyl Acylation of the Tumor Necrosis Factor alpha Precursor on Specific Lysine Residues," The Journal of Experimental Medicine, Oct. 1992, vol. 176 (4), pp. 1053-1062.
Stevenson et al., "The 31-Kda Precursor of Interleukin 1 Alpha is Myristoylated on Specific Lysines Within the 16-Kda 4-Terminal Propiece," Proceedings of the National Academy of Sciences of the United States of America, Aug. 1993, vol. 90 (15), pp. 7245-7249.
Sugii et al., "Performance Improvement in Protein N-Myristoyl Classification By BONSAI with Insignificant Indexing Symbol," Genome Informatics, 2007, vol. 18, pp. 277-286.
Suzuki et al., "Strategy for Comprehensive Identification of Human N-Myristoylated Proteins Using an Insect Cell-Free Protein Synthesis System," Proteomics, May 2010, vol. 10 (9), pp. 1780-1793.
Swerdlow, WHO classification of tumours of haematopoietic and lymphoid tissues. Lyon: International Agency for Research on Cancer; GLOBOCAN 2012. Accessed Apr. 9, 2016 (5 pages) [online]. Retrieved from the Internet:.
Takada et al., "Monounsaturated Fatty Acid Modification of Wnt Protein: Its Role in Wnt Secretion," Development Cell, Dec. 2006, vol. 11 (6), pp. 791-801.
Takamune et al., "Suppression of Human Immunodeficiency Virus Type-1 Production by Coexpression of Catalytic-Region-Deleted N-Myristoyltransferase Mutants," Biological and Pharmaceutical Bulletin, 2010, vol. 33 (12), pp. 2018-2023.
Tate et al., "N-Myristoyltransferase as a Potential Drug Target in Malaria and Leishmaniasis," Parasitology, Jan. 2014, vol. 141 (1), pp. 37-49.
The Affordable Care Act. The Leukemia and Lymphoma Society. accessed on Oct. 30, 2013 The Affordable Care Act (2 pages) [online]. Retrieved from the Internet:.
Thinon et al., "Global Profiling of Co- And Post-Translationally N-Myristoylated Proteomes in Human Cells," Nature Communications, Sep. 2014, vol. 5, 13 pages.
Tomatis et al., "Acyl-Protein Thioesterase 2 Catalizes the Deacylation of Peripheral Membrane-Associated GAP-43," PLoS One, Nov. 2010, vol. 5 (11), pp. e15045.
Toska et al., "Repression of Transcription by WT1-BASP1 Requires the Myristoylation of BASP1 and the PIP2-Dependent Recruitment of Histone Deacetylase," Cell Reports, Sep. 2012, vol. 2 (3), pp. 462-469.
Towler et al., "Amino-Terminal Processing of Proteins by N-myristoylation. Substrate Specificity of N-myristoyl transferase," The Journal of Biological Chemistry, Jan. 1987, vol. 262 (3), pp. 1030-1036.
Towler et al., "Protein Fatty Acid Acylation: Enzymatic Synthesis of an N-Myristoylglycyl Peptide," Proceedings of the National Academy of Sciences of the United States of America, May 1986, vol. 83 (9), pp. 2812-2816.
Towler et al., "Purification and Characterization of Yeast Myristoyl CoA:Protein N-Myristoyltransferase," Proceedings of the National Academy of Sciences of the United States of America, May 1987, vol. 84 (9), pp. 2708-2712.
Traverso et al., "High-Throughput Profiling of N-Myristoylation Substrate Specificity Across Species Including Pathogens," Proteomics, Jan. 2013, vol. 13 (1), pp. 25-36.
Tsai et al., "Chemical Biology of Glycosylphosphatidylinositol Anchors," Angewandte Chemie International Edition in English, Nov. 2012, vol. 51 (46), pp. 11438-11456.
Turnay et al., "Structure-function Relationship in Annexin A13, the Founder Member of the Vertebrate Family of Annexins," The Biochemical Journal, Aug. 2005, vol. 389 (Pt 3), pp. 899-911.
Brazil Patent Application No. 1120150096077, Office Action published Sep. 10, 2019—incl English Translation.
Canadian Patent Application No. 2,842,443, Office Action dated Nov. 15, 2019.
Canadian Patent Application No. 2,890,113, Office Action dated Oct. 10, 2019.
Chinese Patent Application No. 201910841567.4, Office Action dated Sep. 30, 2019—English Translation Not Available.
Korean Patent Application No. 10-2014-7004635, Office Action dated Sep. 6, 2019—incl English Translation Available.
Australian Patent Application No. 2018202839, First Examination Report dated Mar. 29, 2019.
Australian Patent Application No. AU2013337569, Examination Report dated May 2, 2019.
Chinese Patent Application No. CN 201380056950.X, Office Action dated May 22, 2019—English Translation not available.
Korean Patent Application No. 10-2014-7004635, Office Action dated May 27, 2019 English Translation Available.
Beauchamp et al., Targeting N-myristoylation for therapy of B-cell lymphomas. Nat Commun. Oct. 22, 2020;11(1)5348 (46 pages).
Final Office Action issued by the USPTO in U.S. Appl. No. 15/943,068 dated Oct. 30, 2020.
Australian Patent Application No. 2018203395, Examination Report dated Apr. 22, 2020 (3 pages).
Brazilian Patent Application No. 112014001430-2, Office Action dated May 5, 2020—English Translation Available (9 pages total).
Das et al., Inhibition of Protein N-Myristoylation: A Therapeutic Protocol in Developing Anticancer Agents. Curr Cancer Drug Targets. Jul. 2012;12(6) 1-26.
Israel Patent Application No. 230575, Office Action dated Jan. 8, 2020—English Translation Available (7 pages total).
Korean Patent Application No. 10-2015-7014547, Office Action dated Mar. 6, 2020—English Translation Available (18 pages total).
U.S. Appl. No. 15/943,068, Non-Final Office Action dated Apr. 22, 2020 (9 pages).
Canadian Patent Application No. 2,842,443, Office Action dated Jan. 22, 2021.
Canadian Patent Application No. 2,890,113, Office Action dated Jan. 26, 2021.
Chinese Patent Application No. 201910130300 4, Office Action dated Dec. 2, 2020—English Translation Available.
European Patent Application No. 16826961.1, Extended European Search Report dated Dec. 5, 2018.
European Patent Application No. 16826961.1, Communication pursuant to Article 94(3) EPC dated Dec. 4, 2019.
European Patent Application No. 16826961.1, Communication pursuant to Article 94(3) EPC dated Feb. 23, 2021.
Falkenberg et al., "Histone Deacetylases and Their Inhibitors in Cancer, Neurological Diseases and Immune Disorders," Nature Reviews Drug Discovery, Sep. 2014, vol. 13 (9), pp. 673-691.
International Patent Application No. PCT/CA2016/050846, International Preliminary Reporton Patentability dated Jan. 23, 2018.
International Patent Application No. PCT/CA2016/050846, International Search Report and Written Opinion dated Sep. 14, 2016.
Suzuki and Bird., "DNA Methylation Landscapes: Provocative Insights From Epigenomics," Nature Reviews Genetics, Jun. 2008, vol. 9, pp. 465-476.
Japanese Patent Application No. 2018-502095, Office Action dated Jul. 6, 2020—English Translation Available.
Korean Patent Application No. 10-2015-7014547, Office Action dated Feb. 22, 2021—English Translation Available.
Kuang et al., "Genome-wide Identification of Aberrantly Methylated Promoter Associated 1-3 and 32-81 Cpg Islands in Acute Lymphocytic Leukemia," Leukemia, Aug. 2008, vol. 22 (8), pp. 1529-1538.

(56) References Cited

OTHER PUBLICATIONS

Lane et al., "Histone Deacetylase Inhibitors in Cancer Therapy," Journal of Clinical Oncology, Nov. 2009, vol. 27 (32), pp. 5459-5468.

Mackey et al., "N-Myristoyltransferase Proteins in Breast Cancer: Prognostic Relevance and Validation as a New Drug Target," Breast Cancer Research and Treatment, Jan. 2021, 7 pages.

Moore et al., "DNA Methylation and Its Basic Function," Neuropsychopharmacology, 2013, vol. 38, pp. 23-38.

Singapore Patent Application No. SG10201703505V, Search Report and Written Opinion dated Mar. 22, 2021.

U.S. Appl. No. 15/745,578, Restriction Requirement dated Aug. 23, 2019.

U.S. Appl. No. 15/745,578, Non-Final Office Action dated Dec. 28, 2020.

Lueg et al., "N-myristoyltransferase Inhibition Is Synthetic Lethal in MYC-Deregulated Cancers," BioRxiv, Mar. 20, 2021, 25 pages, Retrieved from [URL:https://doi.org/10.1101/2021.03.20.436222].

Chinese Patent Application No. 201910841567.4, Office Action dated Jun. 29, 2021—English Translation Available.

European Patent Application No. 20213908.5, Extended European Search Report dated Jun. 9, 2021.

Goncalves et al., "Discovery of Plasmodium Vivax N-myristoyltransferase Inhibitors: Screening, Synthesis, and Structural Characterization of their Binding Mode," J Med Chem. Apr. 1, 20122;55(7):3578-3582.

Japanese Patent Application No. 2018-502095, Office Action dated Jun. 21, 2021—English Translation Available.

Rackham et al., "Discovery of Novel and Ligand-Efficient Inhibitors of Plasmodium Falciparum and Plasmodium Vivax N-myristoyltransferase," J Med Chem Jan. 1, 2013; 56(1):371-375.

U.S. Appl. No. 15/943,068, Non-Final Office Action dated May 17, 2021.

Wright et al., "Validation of N-myristoyltransferase as an Antimalarial Drug Target Using an Integrated Chemical Biology Approach," Nat Chem. Feb. 2014;6(2):112-121.

* cited by examiner

PANEL A

Rabbit anti-NMT1

Rabbit anti-GAPDH

IM9: B lymphoblast
BL2: Burkitt's lymphoma
CEM: T cell leukemia
Karpas 299: T cell lymphoma
Sup-M2: ALCL DAUDI: Burkitt's lymphoma
Ramos: Burkitt's lymphoma
BJAB: Burkitt's lymphoma
HD-MYZ: Hodgkin lymphoma
KM-H2: Hodgkin lymphoma

PANEL B

IM9: B lymphoblast
BL2: Burkitt's lymphoma
CEM: T cell leukemia
Karpas 299: T cell lymphoma
Sup-M2: ALCL DAUDI: Burkitt's lymphoma
Ramos: Burkitt's lymphoma
BJAB: Burkitt's lymphoma
HD-MYZ: Hodgkin lymphoma
KM-H2: Hodgkin lymphoma

PANEL A

PANEL B

SYNTHETIC LETHALITY AND THE TREATMENT OF CANCER

RELATED APPLICATIONS

This application is a continuation of U.S. patent application Ser. No. 14/234,312, filed Apr. 1, 2014, which is the U.S. national phase of International Application No. PCT/CA2012/000696, filed Jul. 23, 2012, which designated the U.S. and claims priority to U.S. Provisional Application No. 61/510,686, filed Jul. 22, 2011, the contents all of which are hereby incorporated by reference in their entirety.

FIELD OF THE INVENTION

The field of the invention generally relates to compounds, compositions and methods for treatment of cancer.

BACKGROUND OF THE INVENTION

Cancer is a leading cause of death in Canada. The Canadian Cancer Society estimate there will be approximately 170000 new cases of cancer in 2011, and approximately 75000 deaths as a result of cancer.

An emerging approach for the treatment of cancer relates to the concept of synthetic lethality. Two genes (or two gene products) are synthetic lethal if mutation of either alone is compatible with viability but mutation of both leads to death. Put another way, "synthetic lethality" describe situations where a mutation and a drug (for example) together cause a cancer cell's death—either the mutation or the drug would not result in cell death. Targeting a gene (or gene product) that is synthetic lethal to a cancer-relevant mutation should kill only cancer cells and spare normal cells. Synthetic lethality therefore provides a framework for the development of anti-cancer specific agents.

The approach of synthetic lethality to the treatment of cancer is emerging, is not yet a routine approach largely due to the absence identification of synthetic lethal genes (and gene products).

N-myristoylation of proteins is a modification in which myristate (a 14-carbon saturated fatty acid) is covalently attached to the $NH_2$ terminal glycine of a variety of cellular, viral, and onco-proteins (e.g., oncogenic Src-related tyrosine kinases, heterotrimeric G alpha subunits, etc.).

Cellular myristoylated proteins have diverse biological functions in signal transduction and oncogenesis. Modification of proteins by myristoylation is required for the subcellular targeting, protein conformation and biological activity of many important proteins in eukaryotic cells, including those required for signal transduction and regulatory functions important in cell growth. Tyrosine kinases of the Src family (proto-oncogenes) are among the most extensively studied myristoylated proteins.

Myristoylation of proteins is catalyzed N-myristoyltransferase (NMT). NMT is responsible for this activity in eukaryotic cells and works by modifying its polypeptide substrate after the removal of the initiator methionine residue by methionyl aminopeptidase. This modification occurs primarily as a cotranslational process, although myristoylation can also occur post-translationally after proteolytic cleavage of proteins, typically during apoptosis. Two isozymes of the mammalian NMT enzymes have been cloned and are designated NMT1 and NMT2. NMTs play a pro-survival role in cells. The two NMTs are present in all normal cells.

There remains a need for compounds, composition and method for the treatment of cancer.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

In accordance with one aspect of the present invention there is provided compounds and compositions for the treatment of a subject with cancer. There are also provided methods for identifying subject with cancer that are suitable for treatment with the compounds, composition and methods are described herein.

In accordance with one aspect of the present invention, there is provided a method of treating a subject having a cancer deficient in NMT2, comprising: administering to said subject an NMT inhibitor. In a specific example, said NMT inhibitor is a NMT1 inhibitor.

In a specific aspect, said cancer is a lymphoma. In a aspect example, said lymphoma is a B cell lymphoma. In a more specific example, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

In a specific aspect, said NMT inhibitor is a small molecule, an antibody, a peptide fragment, or a nucleic acid.

In a specific aspect, said small molecule is Tris-DBA, HMA, or DDD85646, or a derivative thereof. In a specific aspect, said antibody is a monoclonal antibody or a polyclonal antibody. In a specific aspect, said nucleic acid comprises a dsRNA molecule, a RNAi molecule, miRNA molecule, a ribozyme, a shRNA molecule, or a siRNA molecule.

In a specific aspect, said subject is a human subject.

In another aspect of the present invention, the method further comprises administering a chemotherapeutic agent. In a specific example, said chemotherapeutic agent is CHOP, GAP-BOP, m-BACOD, ProMACE-MOPP, ProMACE-CytaBOM, MACOP-B, IMVP-16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

In another aspect of the present invention, there is provided a method of treating a subject having cancer, comprising: measuring a sample from said subject to determine whether said sample is deficient in NMT2; and administering an inhibitor of NMT to said subject when said sample is deficient in NMT2. In a specific example, said NMT inhibitor is a NMT1 inhibitor.

In a specific aspect, said NMT inhibitor is a NMT1 inhibitor.

In a specific aspect, said cancer is a lymphoma. In a specific aspect, said lymphoma is a B cell lymphoma. In a more specific aspect, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

In a specific aspect, said NMT inhibitor is a small molecule, an antibody, a peptide fragment, or a nucleic acid.

In a specific aspect, said small molecule is Tris-DBA, HMA, or DDD85646, or a derivative thereof. In a specific aspect, said antibody is a monoclonal antibody or a polyclonal antibody. In a specific aspect, said nucleic acid comprises a dsRNA molecule, a RNAi molecule, miRNA molecule, a ribozyme, a shRNA molecule, or a siRNA molecule.

In a specific aspect, said subject is a human subject.

In another aspect of the present invention, the method further comprises administering a chemotherapeutic agent. In a specific example, said chemotherapeutic agent is CHOP, GAP-BOP, m-BACOD, ProMACE-MOPP, ProMACE-CytaBOM, MACOP-B, IMVP-16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

In another aspect, measuring of said sample is carried out using quantitative fluorescence activated cell sorting, enzyme linked immunosorbent assay, immunohistochemistry, quantitative immunohistochemistry, fluorescence resonance energy transfer, Forster resonance energy transfer, biomolecular fluorescence complementation, mass spectrometry, immunoblot assay or coimmunoprecipitation assay.

In another aspect of the present invention, there is provided a kit for treating cancer in of treating a subject having a cancer deficient in NMT2, comprising: an NMT inhibitor; and instructions for the use thereof. In one example, said NMT inhibitor is a NMT1 inhibitor.

In a specific aspect, said cancer is a lymphoma. In a specific aspect, said lymphoma is a B cell lymphoma. In a more specific aspect, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

In a specific aspect, said NMT inhibitor is a small molecule, an antibody, a peptide fragment, or a nucleic acid.

In a specific aspect, said small molecule is Tris-DBA, HMA, or DDD85646, or a derivative thereof. In a specific aspect, said antibody is a monoclonal antibody or a polyclonal antibody. In a specific aspect, said nucleic acid comprises a dsRNA molecule, a RNAi molecule, miRNA molecule, a ribozyme, a shRNA molecule, or a siRNA molecule.

In a specific aspect, said subject is a human subject.

In another aspect of the present invention, the method further comprises administering a chemotherapeutic agent. In a specific example, said chemotherapeutic agent is CHOP, GAP-BOP, m-BACOD, ProMACE-MOPP, ProMACE-CytaBOM, MACOP-B, IMVP-16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

In another aspect of the present invention, there is provided a use of an inhibitor NMT for treating a subject having a cancer deficient in NMT2. In a specific example, said NMT inhibitor is a NMT1 inhibitor.

In a specific aspect, said cancer is a lymphoma. In a specific aspect, said lymphoma is a B cell lymphoma. In a more specific aspect, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

In a specific example, said NMT inhibitor is a small molecule, an antibody, a peptide fragment, or a nucleic acid.

In a specific example, said small molecule is Tris-DBA, HMA, or DDD85646, or a derivative thereof. In a specific aspect, said antibody is a monoclonal antibody or a polyclonal antibody. In a specific aspect, said nucleic acid comprises a dsRNA molecule, a RNAi molecule, miRNA molecule, a ribozyme, a shRNA molecule, or a siRNA molecule.

In a specific aspect, said subject is a human subject.

In another aspect of the present invention, the method further comprises administering a chemotherapeutic agent. In a specific example, said chemotherapeutic agent is CHOP, GAP-BOP, m-BACOD, ProMACE-MOPP, ProMACE-CytaBOM, MACOP-B, IMVP-16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

In another aspect of the present invention, there is provided a use of an inhibitor NMT for the preparation of a medicament for treating a subject having a cancer deficient in NMT2.

In a specific aspect, said NMT inhibitor is a NMT1 inhibitor.

In a specific aspect, said cancer is a lymphoma. In a specific aspect, said lymphoma is a B cell lymphoma. In a more specific aspect, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

In a specific aspect, said NMT inhibitor is a small molecule, an antibody, a peptide fragment, or a nucleic acid.

In a specific aspect, said small molecule is Tris-DBA, HMA, or DDD85646, or a derivative thereof. In a specific aspect, said antibody is a monoclonal antibody or a polyclonal antibody. In a specific aspect, said nucleic acid comprises a dsRNA molecule, a RNAi molecule, miRNA molecule, a ribozyme, a shRNA molecule, or a siRNA molecule.

In a specific aspect, said subject is a human subject.

In another aspect of the present invention, the method further comprises administering a chemotherapeutic agent. In a specific example, said chemotherapeutic agent is CHOP, GAP-BOP, m-BACOD, ProMACE-MOPP, ProMACE-CytaBOM, MACOP-B, IMVP-16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

In another aspect of the present invention, there is provided a use of NMT2 as a marker for one or more of diagnosis, prognosis, classifying, or monitoring of cancer in a subject.

In another aspect of the present invention, there is provided a use of protein myristoylation as a marker for one or more of diagnosis, prognosis, classifying or monitoring cancer in a subject.

In another aspect of the present invention, there is provided a use of protein acylation as a marker for one or more of diagnosis, prognosis, classifying or monitoring cancer in a subject.

In a specific aspect, said cancer is lymphoma.

In a specific aspect, said lymphoma is B cell lymphoma.

In a specific aspect, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

In a specific aspect, said marker is measured using an assay selected from immunoassays or nucleic acid detection, or protein activity.

BRIEF DESCRIPTION OF THE DRAWINGS

Embodiments of the present invention will now be described, by way of example only, with reference to the attached Figures, wherein.

Figure 1:
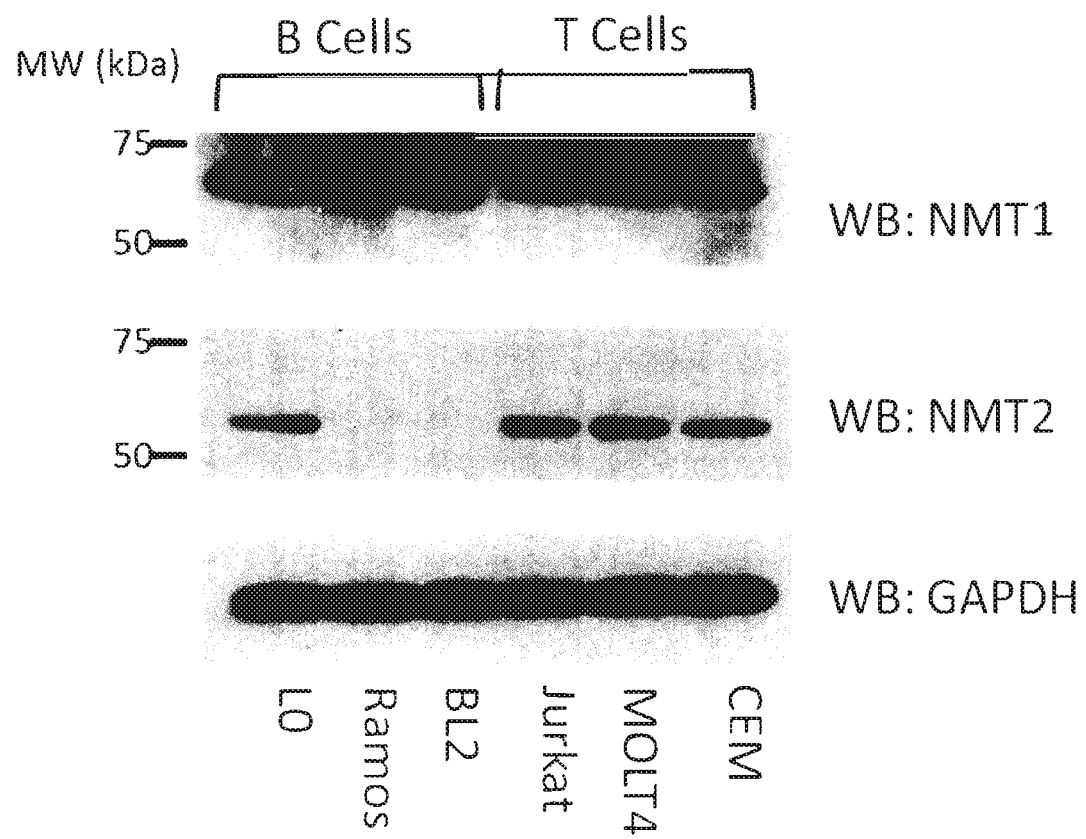
FIG. 1 depicts immunoblot analysis of NMT1 and NMT2 expression in one type of normal B cells (L0) and various B cell lymphomas and T cell leukemias.

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, parts have been omitted from some figures of the drawings.

DETAILED DESCRIPTION

As will be described in more detail below, there is described herein compounds, composition and methods for the treatment of a subject with cancer. There are also described here methods for identifying subject with cancer that are suitable for treatment with the compounds, composition and methods are described herein. There are also described here methods for identifying subject with cancer.

The present application provides methods and compositions for the treatment of NMT deficient cancers. NMT-deficient cancers include cancers deficient in NMT2 or NMT1. In a specific example, the NMT deficient cancer is a NMT2 deficient cancer.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. Cancer cells may be in the form of a tumour, but such cells may also exist alone within a subject, or may be a non-tumorigenic cancer cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

In a specific example of the present disclosure, the cancer is lymphoma.

The term "lymphoma" as used herein refers to a malignant growth of B or T cells in the lymphatic system. "Lymphoma" includes numerous types of malignant growths, including Hodgkin's Lymphoma and non-Hodgkin's lymphoma. The term "non-Hodgkin's Lymphoma" as used herein, refers to a malignant growth of B or T cells in the lymphatic system that is not a Hodgkin's Lymphoma (which is characterized, e.g., by the presence of Reed-Sternberg cells in the cancerous area). Non-Hodgkin's lymphomas encompass over 29 types of lymphoma, the distinctions between which are based on the type of cancer cells.

In a more specific example of the present disclosure, the cancer is a B-lymphoma.

Thus, in one embodiment, the compounds, compositions and methods of the disclosure are suitable for the treatment of a subject with B cell lymphoma.

Examples of B-cell lymphomas include, but are not limited to, for example, follicular lymphoma, diffuse large B-cell lymphoma, mantle cell lymphoma, B-CLL/SLL, immunocytoma/Waldenstrom's, and MALT-type/monocytoid B cell lymphoma. Also contemplated are the treatment of pediatric lymphomas such as Burkitt's lymphoma, diffuse large B-cell lymphoma, follicular lymphoma, precursor B-LBL, precursor T-LBL, and anaplastic large cell lymphoma.

The term "subject", as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The term "treatment" or "treat" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early cancer, for example an early stage lymphoma, can be treated to prevent progression or alternatively a subject in remission can be treated with a compound or composition described herein to prevent recurrence.

Figure 4:
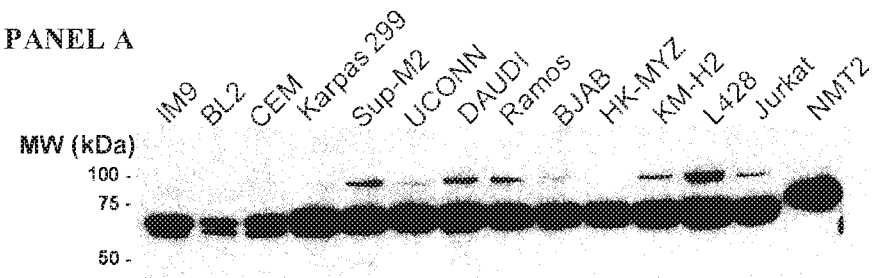
FIG. 4 are immunoblots depicting lymphoma cell lines probed with antibodies against NMT1 and NMT2.
Figure 4:
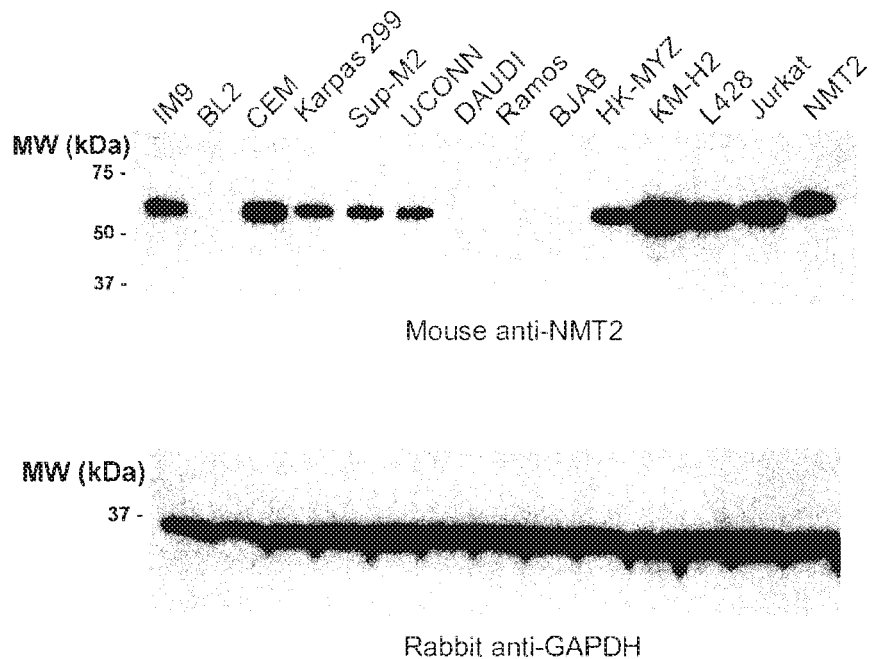

It is shown herein that B cell lymphoma cells express NMT1, but not NMT2. This is in contrast to the leukemic and other cells tested which express both NMT1 and NMT2. (As shown in FIGS. 1 and 4)

It is further shown herein that B lymphoma cells are sensitive to inhibition of cell viability by NMT inhibitors.

Figure 2:
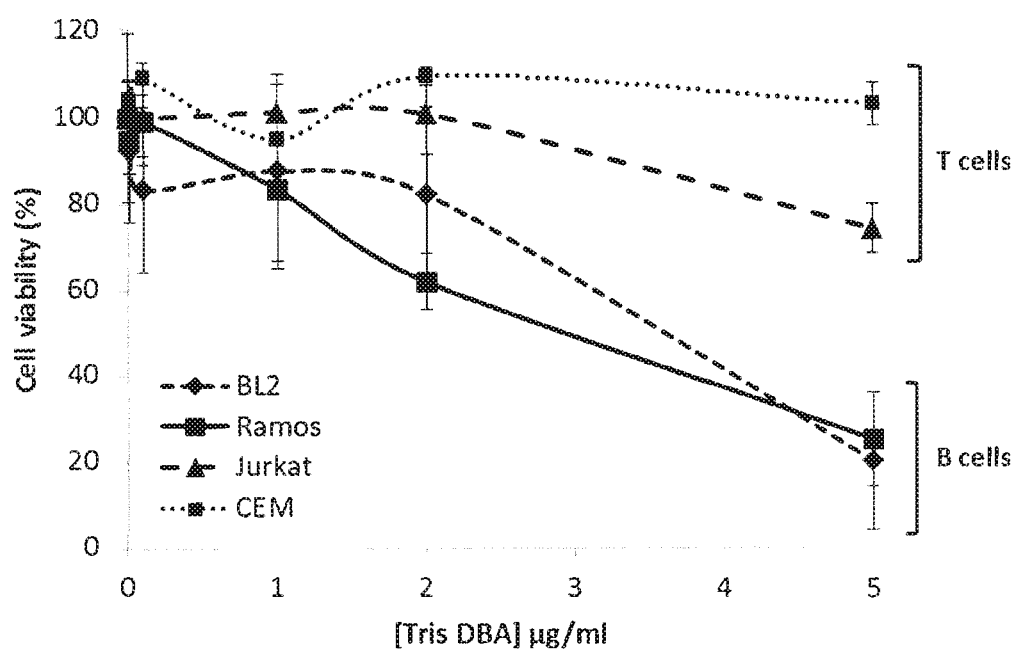
FIG. 2 is a graph illustrating sensitivity of various normal cells and various B cell lymphomas and T cell leukemias to the NMT inhibitors tris-dibenzylideneacetone-dipalladium (Tris-DBA)

In one example, the NMT inhibitor is tris-dibenzylideneacetone-dipalladium (Tris-DBA) (FIG. 2)

In other examples, the NMT inhibitor 2-hydroxymyristae (HMA) is used to inhibit B lymphoma cells.

Figure 5:
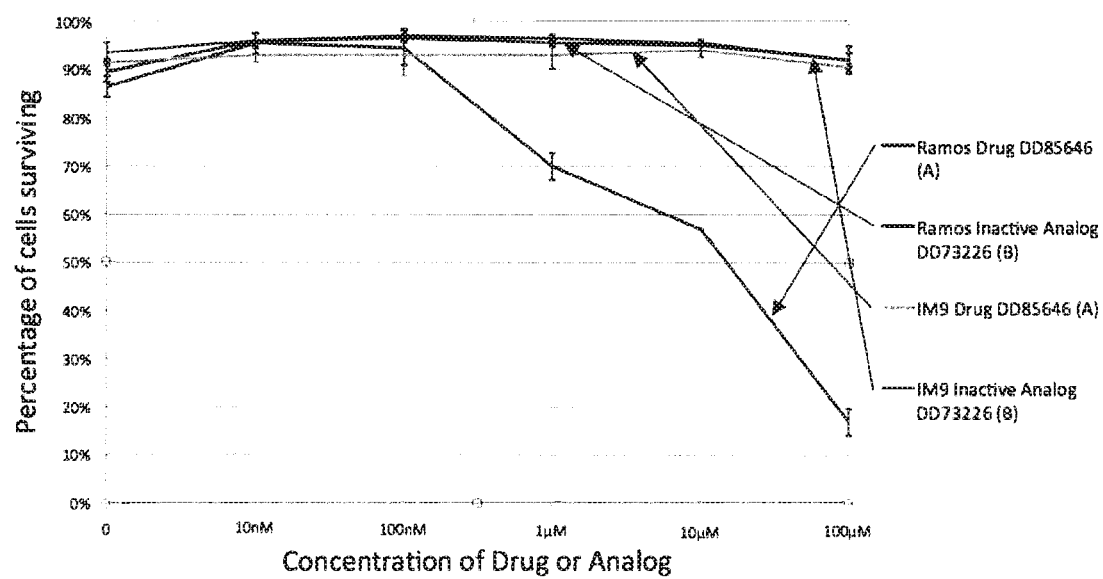
FIG. 5 is a line graph showing the sensitivity of NMT inhibitors on a Burkitt's Lymphoma cell line in comparison to an immortalized normal B lymphocytic cell line.

In yet another example, the pyrazole sulphonamide inhibitor of *T. brucie* NMT [J. A. Frearson et al (2010) Nature. 464.728-723)] (DDD85646) is used to inhibit B lymphoma cells. (FIG. 5).

In a specific example, treatment of a subject with B lymphoma comprises administering said subject with an NMT inhibitor.

NMT inhibitor compounds or derivatives may be used in the present invention for the treatment of NMT2 deficient cancer.

There term "deficient" as used herein refers broadly to inhibition, reduction or elimination of (as compared to wild type or control samples), for example, NMT synthesis, levels, activity, or function, as well as inhibition of the induction or stimulation of synthesis, levels, activity, or function of the protein of NMT (for example NMT 1 or NMT2). The term also refers to any metabolic or regulatory pathway which can regulate the synthesis, levels, activity, or function of NMT. The term includes also includes inhibition, reduction or elimination resulting form binding with other molecules and complex formation. Therefore, the term "NMT deficient" refers to that which results in the inhibition, reduction, or elimination of protein function or protein pathway function. However, the term does not imply that each and every one of these functions must be inhibited at the same time.

In some examples, a cancer may be identified as being deficient in NMT by determining the presence of a mutation in a NMT gene. Such methods of nucleic acid detection and amplification are well known to the skilled worker.

For example the nucleic acid to be amplified may be from a biological sample. Various methods (such as phenol and chloroform extraction) of extraction are suitable for isolating the DNA or RNA. Nucleic acid extracted from a sample can be amplified using nucleic acid amplification techniques well known in the art. Non limiting examples include chain reaction (PCR), reverse transcriptase polymerase chain reaction (RT-PCR), nested PCR, ligase chain reaction, amplifiable RNA reporters, Q-beta replication, transcription-based amplification, boomerang DNA amplification, strand displacement activation, cycling probe technology, isothermal nucleic acid sequence based amplification (NASBA), or other sequence replication assays or signal amplification assays may also be used.

Methods of amplification are well-known in the art. Some methods employ reverse transcription of RNA to cDNA.

In one example, PCR is used to amplify a target sequence of interest, e.g., a NMT2 sequence.

Nucleic acids may be amplified prior to detection or may be detected directly during an amplification step, e.g., "real-time" methods. In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

The level of gene expression can be determined by assessing the amount of NMT2 mRNA in a sample. Methods of measuring mRNA in samples are known in the art. To measure mRNA levels, the cells in the samples can be lysed and the levels of mRNA in the lysates or in RNA purified or semi-purified from lysates can be measured by any variety of methods familiar to those in the art. Such methods include, without limitation, hybridization assays using detectably labeled DNA or RNA probes, e.g., northern blotting, or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled, e.g., fluorescent, or enzyme-labeled, DNA or RNA probes. Additional methods for quantifying mRNA include RNA protection assay ("RPA"), cDNA and oligonucleotide microarrays, representation difference analysis ("RDA"), differential display, EST sequence analysis, serial analysis of gene expression ("SAGE"), and multiplex ligation-mediated amplification with the Luminex FlexMAP ("LMF").

Amplification can also be monitored using "real-time" methods. Real time PCR allows for the detection and quantitation of a nucleic acid target. Typically, this approach to quantitative PCR utilizes a fluorescent dye, which may be a double-strand specific dye, such as SYBR Green® I. Alternatively, other fluorescent dyes, e.g., FAM or HEX, may be conjugated to an oligonucleotide probe or a primer. Various instruments capable of performing real time PCR are known in the art. The fluorescent signal generated at each cycle of PCR is proportional to the amount of PCR product. A plot of fluorescence versus cycle number is used to describe the kinetics of amplification and a fluorescence threshold level is used to define a fractional cycle number related to initial template concentration. When amplification is performed and detected on an instrument capable of reading fluorescence during thermal cycling, the intended PCR product from non-specific PCR products can be differentiated using melting analysis. By measuring the change in fluorescence while gradually increasing the temperature of the reaction subsequent to amplification and signal generation it may be possible to determine the ($\Delta$ct) of the intended product(s) as well as that of the nonspecific product.

The methods may include amplifying multiple nucleic acids in sample, also known as "multiplex detection" or "multiplexing." As used herein, the term "multiplex PCR" refers to PCR, which involves adding more than one set of PCR primers to the reaction in order to detect and quantify multiple nucleic acids, including nucleic acids from one or more target gene markers. Furthermore, multiplexing with an internal control, e.g., 18s rRNA, GADPH, or .beta.-actin) provides a control for the PCR without reaction.

In some examples, a cancer may be identified as being deficient in NMT by determining epigenetic inactivation a NMT gene, or loss of the loss of protein function.

In some examples, a cancer may be identified as being deficient in NMT by determining the activity of NMT (including NMT1 or NMT2) in a sample of cells from a subject. Activity may be determined relative to a control, for example in the case of defects in cancer cells, relative to non-cancerous cells, preferably from the same tissue. Thus, a cancer deficient in NMT may have reduced or eliminated NMT activity and/or expression. The activity of NMT may be determined by using techniques well known in the art. In these examples, a cancer deficient in NMT has a reduced or eliminated activity.

In some examples, a cancer may be identified as NMT deficient by determining the amount, concentration and/or levels of NMT protein.

In some examples, a cancer may be identified as NMT deficient by determining the amount of myristoylated proteins in a biological sample from a subject with cancer, or suspected of having cancer. In this example, the presence, absence or amount of myristoylated protein can be determined, for example, using click chemistry using appropriate fatty acid analogs. Non-limiting methods are described herein, in the Materials and Method. Alternate methods of determining the presence, absence, or amount of myristoylated proteins will be known to the skilled worker. A sample which has a reduced amount myristoylated protein in a sample (optionally as compared to a control) is indicative of an NMT deficient sample, or NMT deficient cancer.

In some examples, a cancer may be identified as NMT deficient by determining the amount of the amount of acylation of proteins in a biological sample from a subject with cancer, or suspect of having cancer. In this example, the presence, absence or amount of acylation of proteins can be determined. Such methods would be know to the skilled worker. A sample which as a reduced amount of acylation of proteins in a sample (optionally as compared to a control) is indicative of an NMT deficient sample, or NMT deficient cancer.

In some examples, a cancer may be identified as a NMT deficient by determining the presence of one or more sequence variations such as mutations and polymorphisms may include a deletion, insertion or substitution of one or more nucleotides, relative to the wild-type nucleotide sequence. The one or more variations may be in a coding or non-coding region of the nucleic acid sequence and, may reduce or abolish the expression or function of NMT. Thus, the variant nucleic acid may encode a variant polypeptide which has reduced or abolished activity or may encode a wild-type polypeptide which has little or no expression within the cell, for example through the altered activity of a regulatory element.

A variety of methods may be used for determining the presence or absence of a particular nucleic acid sequence in a sample obtained from a subject.

In some examples, a cancer may be identified as NMT-deficient by assessing the level of expression or activity of a positive or negative regulator of NMT of a component of the NMT pathway. Expression levels may be determined, for example, by immunoassays, such as immunoblotts and ELISA, and nucleic acid detection methods, such as RT-PCR, nanostring technology, RNA-seq, nucleic acid hybridisation or karyotypic analysis.

In some examples, a cancer may be identified as being deficient in NMT by determining the presence in a cell sample from the individual of one or more variations, for example, polymorphisms or mutations in NMT.

Mutations and polymorphisms associated with cancer may also be detected at the protein level by detecting the presence of a variant (i.e. a mutant or allelic variant) polypeptide.

In another example, there is provided a method a treating a subject with cancer, wherein said cancer comprises cancer cells which are deficient in NMT2, comprising administering to said subject an NMT inhibitor and/or an NMT1 inhibitor.

The term "inhibit" or "inhibitor" as used herein, refers to any method or technique which inhibits protein synthesis, levels, activity, or function, as well as methods of inhibiting the induction or stimulation of synthesis, levels, activity, or function of the protein of interest, for example NMT2. The term also refers to any metabolic or regulatory pathway which can regulate the synthesis, levels, activity, or function of the protein of interest. The term includes binding with other molecules and complex formation. Therefore, the term "inhibitor" refers to any agent or compound, the application of which results in the inhibition of protein function or protein pathway function. However, the term does not imply that each and every one of these functions must be inhibited at the same time.

In another example, there is provided a method of treating a subject with cancer, wherein said cancer comprises cancer cells deficient in NMT1, comprising administering to said subject an NMT inhibitor and/or an NMT2 inhibitor.

In some examples, treatment methods comprise administering to a subject a therapeutically effective amount of a compound described herein and optionally consists of a single administration, or alternatively comprises a series of applications. In a specific example, said compound is a NMT inhibitor, an NMT1 inhibitor and/or an NMT2 inhibitor.

In a more specific example, the NMT inhibitor is Tris-DBA, HMA, DDD85646, or derivatives thereof.

In other examples, the compounds and/or compositions are provided in a pharmaceutically effect amount suitable for administration to a subject.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

The compounds and compositions are provided in a pharmaceutically acceptable form.

The term "pharmaceutically acceptable" as used herein includes compounds, materials, compositions, and/or dosage forms which are suitable for use in contact with the tissues of a subject without excessive toxicity, irritation, allergic response, or other problem or complication, commensurate with a reasonable benefit/risk ratio. Each carrier, excipient, etc. is also be "acceptable" in the sense of being compatible with the other ingredients of the formulation.

The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

A compound or composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection.

The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising compounds disclosed herein may be used in the methods described herein in combination with standard chemotherapeutic regimes or in conjunction with radiotherapy.

In the case of lymphoma in a patient, know treatments are dependent upon the subject being treated, the type of disease, and its stage. Existing treatment modalities for lymphoma are known to the skilled worker. Accordingly, there know treatments may be used together with the NMT inhibitors disclosed herein.

Common drug combinations for use in treating lymphomas include, but are not limited, to CHOP (i.e., cyclophosphamide, doxorubicin, vincristine, and prednisone), GAP-BOP (i.e., cyclophosphamide, doxorubicin, procarbazine, bleomycin, vincristine, and prednisone), m-BACOD (i.e., methotrexate, bleomycin, doxorubicin, cyclophosphamide, vincristine, dexamethasone, and leucovorin), ProMACE-MOPP (i.e., prednisone, methotrexate, doxorubicin, cyclophosphamide, etoposide, leucovorin with standard MOPP), ProMACE-CytaBOM (prednisone, doxorubicin, cyclophosphamide, etoposide, cytarabine, bleomycin, vincristine, methotrexate, and leucovorin), and MACOP-B (methotrexate, doxorubicin, cyclophosphamide, vincristine, prednisone, bleomycin, and leucovorin). For relapsed aggressive non-Hodgkin's lymphoma the following chemotherapy drug combinations may be used with the compounds and compositions described herein: IMVP-16 (i.e., ifosfamide, methotrexate, and etoposide), MIME (i.e., methyl-gag, ifosfamide, methotrexate, and etoposide), DHAP (i.e., dexamethasone, −16 high dose cytarabine, and cisplatin), ESHAP (i.e., etoposide, methylprednisone, high dosage cytarabine, and cisplatin), CEFF(B) (i.e., cyclophosphamide, etoposide, procarbazine, prednisone, and bleomycin), and CAMP (i.e., lomustine, mitoxantrone, cytarabine, and prednisone).

Treatment for salvage chemotherapy used for certain lymphomas such as for relapsed, resistant Hodgkin's Disease include but are not limited to VABCD (i.e., vinblastine, doxorubicin, dacarbazine, lomustine and bleomycin), ABDIC (i.e., doxorubicin, bleomycin, dacarbazine, lomustine, and prednisone), CBVD (i.e., lomustine, bleomycin, vinblastine, dexamethasone), PCVP (i.e., vinblastine, procarbazine, cyclophosphamide, and prednisone), CEP (i.e., lomustine, etoposide, and prednimustine), EVA (i.e., etoposide, vinblastine, and doxorubicin), MOPLACE (i.e., cyclophosphamide, etoposide, prednisone, methotrexate, cytaravine, and vincristine), MIME (i.e., methyl-gag, ifosfamide, methotrexate, and etoposide), MINE (i.e., mitoquazone, ifosfamide, vinorelbine, and etoposide), MTX-CHOP (i.e., methotrexate and CHOP), CEM (i.e., lomustine, etoposide, and methotrexate), CEVD (i.e., lomustine, etoposide, vindesine, and dexamethasone), CAVP (i.e., lomustine, melphalan, etoposide, and prednisone), EVAP (i.e., etoposide, vinblastine, cytarabine, and cisplatin), and EPOCH (i.e., etoposide, vincristine, doxorubicin, cyclophosphamide, and prednisone).

It will be appreciated that alternate methods to inhibit NMT1 or NMT2 may be used in a synthetic lethal strategy for the treatment of cancer, and in particular the treatment of B cell lymphoma. For example, expression of NMT1 or NMT2 may be inhibited using anti-sense or RNAi technology. The use of these approaches to down-regulate gene expression and/or protein activity is known to the skilled worker.

In another embodiment of the present disclosure there is provided a method for determining the benefit of NMT2-inhibitor and/or NMT1-inhibitor treatment of a patient.

In one example, a method of the present disclosure comprises qualitatively or quantitatively determining, analyzing or measuring a sample from a subject with cancer, or suspected of having cancer, for the presence or absence, or amount or concentration, of NMT1 and/or NMT2.

In another example, a method of the present disclosure comprises qualitatively or quantitatively determining, analyzing or measuring a sample from a subject with cancer, or suspected of having cancer, for the presence or absence, or amount or concentration, of myristolayted proteins.

In another example, a method of the present disclosure comprises qualitatively or quantitatively determining, analyzing or measuring a sample from a subject with cancer, or suspect of having cancer, for the presence or absence, or amount of concentration of acylated proteins.

The term "sample" as used herein refers to any sample from a subject, including but not limited to a fluid, cell or tissue sample that comprises cancer cells, or which is suspected of containing cancer cells, which can be assayed for gene expression levels, proteins levels, enzymatic activity levels, and the like. The sample may include, for example, a blood sample, a fractionated blood sample, a bone marrow sample, a biopsy, a frozen tissue sample, a fresh tissue specimen, a cell sample, and/or a paraffin embedded section, material from which RNA can be extracted in sufficient quantities and with adequate quality to permit measurement of relative mRNA levels, or material from which polypeptides can be extracted in sufficient quantities and with adequate quality to permit measurement of relative polypeptide levels.

The determination, analysis or measurement of NMT1 or NMT2, or the presence or absence of NMT1 and/or NMT2 can be correlated with the benefit of NMT1-inhibitor or NMT2-inhibitor treatment of cancer in the patient.

The determination, analysis or measurement of myristoylated proteins, or the presence or absence of myristoylated proteins can be correlated with the benefit of NMT1-inhibitor or NMT2-inhibitor treatment of cancer in the patient.

In a specific example, antibodies of the present invention are immunoreactive or immunospecific for, and therefore specifically and selectively bind to a protein of interest, for example the protein NMT1 or NMT2. In one example, antibodies which are immunoreactive and immunospecific for human NMT1 or NMT2 can be used. Antibodies for human NMT1 or NMT2 are preferably immunospecific. The term "antibody" and "antibodies" includes, but is not limited to, monoclonal and polyclonal antibodies.

In another example, antibodies of the present invention are immunoreactive or immunospecific for, and therefore specifically and selectively bind to both NMT1 and NMT2 protein. In this example, antibodies which are immunoreactive and immunospecific for both human NMT1 and NMT2 can be used. Antibodies for human NMT1 and NMT2 are preferably immunospecific. In this example, and owing to the different molecular mass of NMT1 and NMT2, it is possible identify the presence or absence of both proteins using a single antibody, using, for example SDS-PAGE and immunoblotting. The term "antibody" and "antibodies" includes, but is not limited to, monoclonal and polyclonal antibodies.

The term "binds specifically" refers to high avidity and/or high affinity binding of an antibody to a specific polypeptide e.g., an epitope of NMT1 or NMT2. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at weak, yet detectable, level. Such weak binding, or background binding, is readily discernable from the specific antibody binding to the compound or polypeptide of interest, e.g., by use of appropriate controls, as would be known to the worker skilled in the art.

In one example, a sample containing cancerous cells or suspected as containing cancerous cells is obtained from a subject with cancer. Collection of such a sample is well known to the skilled worker. In a specific example, the sample is a blood sample. Methods of obtaining a sample, processing and/or storage of such a sample are also well known to the skilled worker.

In a specific example, the detection, analysis or measurement of NMT1 or NMT2 protein within a sample is carried out using immunohistochemistry. It will be clear to the skilled worker that other immuno assays, both qualitative or quantitative, may be used in the present invention.

Other examples that may be used in the detection, analysis or measurement of NMT1 or NMT2 include, but are not limited to, immunoblotting, ELISA, indirect immuno-fluorescence, multiplexing bead technology, immunoprecipitation and mass spectrometry from sample obtain from the subject. In practice, in the example in which a patient sample is determined to have low or absent NMT2 staining, the subject is considered a good candidate for NMT-inhibitor therapy.

In another example, a method of the present disclosure comprises qualitatively or quantitatively determining, analyzing or measuring the activity of NMT1 and/or NMT2 protein activity in biological sample from a subject with cancer patient for the presence or absence or amount of NMT1 and/or NMT2 activity. In this example, the uses of substrates (natural or synthetic) of NMT1 or NMT2 are used to identify a sample in which NMT1 or NMT2 activity is present, absent, or the amount thereof.

In practice, in the example in which a subject sample is determined to be NMT2 deficient, the subject is considered a good candidate for administration on an NMT inhibitor.

In practice, in the example in which a patient sample is determined to have low or absent NMT2 activity, the subject is considered a good candidate for administration on an NMT inhibitor.

In practice, in the example in which a patient sample is determined to have low or absent amount of myristoylated protein, the subject is considered a good candidate for administration on an NMT inhibitor.

In practice, in the example in which a subject sample is determined to have a low or absent amount of acylated protein, the subject is considered a good candidate for administration on an NMT inhibitor.

In another example, a method of the present disclosure comprises identifying a mutation, deletion, or the like, in the NMT1 or NMT2 gene in a sample from a subject with cancer or suspect of having cancer. Wherein, said mutation, deletion, or the like, in NMT1 or NMT2 gene results in a loss of diminishment of NMT1 or NMT2 protein activity in cancer cells within said sample. Methods of identifying such mutations, deletions, or the like, in NMT1 or NMT2 are known to the skilled worker, and include, but are not limited to, RFLP, RT-PCT, microarray analysis, and/or any suitable type of DNA sequencing. In practice, in the example in which a patient sample is determined to have a mutation, deletion, or the like, in NMT2 which results in a low or absent NMT2 protein activity, the subject is considered a good candidate for NMT-inhibitor therapy.

In another example, a method of the present disclosure comprises identifying a mutation, deletion, or the like, in the NMT1 or NMT2 mRNA in a sample from a subject with cancer or suspect of having cancer. Wherein, said mutation, deletion, or the like, in NMT1 or NMT2 mRNA results in a loss of diminishment of NMT1 or NMT2 protein activity in cancer cells within said sample. Methods of identifying such mutations, deletions, or the like, in NMT1 or NMT2 mRNA are known to the skilled worker, and include, but are not limited to, Northern blotting, RT-PCR, microarray analysis, and/or any suitable type of mRNA sequencing. In practice, in the example in which a patient sample is determined to have a mutation, deletion, or the like, in NMT2 mRNA which results in a low or absent NMT2 protein activity, the subject is considered a good candidate for NMT-inhibitor therapy.

In another example, a method of the present disclosure, there is provided a method for the treatment of a subject suffering from cancer, associated with a defect in NMT1 or NMT2, comprising administering to said subject an inhibitor of NMT.

Examples of inhibitors include, but are not limited to, small molecules, antibodies, peptide fragments, and/or nucleic acid molecules.

Specific examples of small molecules include Tris-DBA, HMA, DDD85646, and their derivatives. The term "derivatives" as used herein includes, but is not limited to, salts, coordination complexes, esters such as in vivo hydrolysable esters, free acids or bases, hydrates, prodrugs or lipids, coupling partners.

Peptide fragments may be prepared wholly or partly by chemical synthesis that active site of NMT1. Peptide fragments can be prepared according to established, standard liquid or solid-phase peptide synthesis methods, which will be known to the skilled worker.

Nucleic acid inhibitors, or the complements thereof, inhibit activity or function by down-regulating production of active polypeptide. This can be monitored using conventional methods well known in the art, for example by screening using real time PCR as described in the examples.

Examples of nucleic acid inhibitors include anti-sense or RNAi technology, the use of which is to down-regulate gene expression is well-established in the art. Anti-sense oligonucleotides may be designed to hybridise to the complementary sequence of nucleic acid, pre-mRNA or mature mRNA, interfering with the production of the base excision repair pathway component so that its expression is reduced or completely or substantially completely prevented. In addition to targeting coding sequence, anti-sense techniques may be used to target control sequences of a gene, e.g. in the 5' flanking sequence, whereby the anti-sense oligonucleotides can interfere with expression control sequences.

An alternative to anti-sense is to use a copy of all or part of the target gene inserted in sense, that is the same, orientation as the target gene, to achieve reduction in expression of the target gene by co-suppression.

Additionally, double stranded RNA (dsRNA) silencing may be used. dsRNA mediated silencing is gene specific and is often termed RNA interference (RNAi).

In another example, nucleic acid is used which on transcription produces a ribozyme, able to cut nucleic acid at a specific site and therefore also useful in influencing NMT.

In yet another example, small RNA molecules may b e employed to regulate gene expression. These include targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

In yet another example, the expression of a short hairpin RNA molecule (shRNA) in the cell may be used. A shRNA consists of short inverted repeats separated by a small loop sequence. One inverted repeat is complimentary to the gene target. In the cell the shRNA is processed by DICER into a siRNA which degrades the target NMT gene mRNA and suppresses expression. In a preferred embodiment the shRNA is produced endogenously (within a cell) by transcription from a vector.

A defect in NMT1 or NMT2 is a NMT1 or NMT2 deficient phenotype which may be deficient in a component of a NMT1 or NMT2 mediated pathway i.e., expression of activity of a component of the pathway may be reduced or abolished in the cancer cell relative to control cells. In some embodiments, the cancer cell may be deficient in NMT1 or NMT2 i.e., expression of activity of NMT1 or NMT2 may be reduced or abolished in the cancer cell relative to control cells.

Accordingly, there is provided the use of NMT2 as a marker for one or more of diagnosis, prognosis, classifying, or monitoring of cancer in a subject. In some examples, NMT2 is said measured using an assay selected from immunoassays or nucleic acid detection, or protein activity.

There is also provided the use of protein myristoylation as a marker for one or more of diagnosis, prognosis, classifying or monitoring cancer in a subject.

There is also provided the use of protein acylation as a marker for one or more of diagnosis, prognosis, classifying or monitoring cancer in a subject.

In some example, said cancer is lymphoma. In more specific examples, said lymphoma is B cell lymphoma. In more specific examples, said B cell lymphoma is follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, or anaplastic large cell lymphoma.

Methods of the invention are conveniently practiced by providing the compounds and/or compositions used in such method in the form of a kit. Such a kit preferably contains the composition. Such a kit preferably contains instructions for the use thereof.

To gain a better understanding of the invention described herein, the following examples are set forth. It should be understood that these example are for illustrative purposes only. Therefore, they should not limit the scope of this invention in any way.

EXAMPLES

In the following examples, standard methodologies were employed, as would be appreciated by the skilled worker.

Materials and Methods

Antibodies and Reagents.

Tris dibutylbenzinylidene acetone paladium (TrisDBA) was a kind gift of Dr. Arbiser (U. Alabama). DDD85646 was synthesised as described [J. A. Frearson et al (2010) Nature. 464.728-723)] and was obtained from Dr. David Gray and Paul Wyatt, Dundee University)

Mouse anti-NMT1 (clone 14; 1:1000) and mouse anti-NMT2 (clone 30; 1:2000) antibodies were from BD Biosciences, San Jose, Calif., USA. Rabbit anti-NMT1 (polyclonal, 1:3000) was purchased from Proteintech, Chicago, Ill., USA. Rabbit anti-GFP (1:20,000), anti-PARP-1 (1:5000), anti-GAPDH (1:5000) and anti-c-terminal PAK2 (1:2000) antibodies were from Eusera (www.euscra.com). Edmonton, AB, Canada. Mouse anti-α-tubulin (1:15,000) and rabbit-anti-V5 (1:10.000) antibodies were purchased from Sigma Aldrich. St. Louis, Mo., USA. Mouse anti-His (1:2000) was from Qiagen, Germany. Rabbit anti-cleaved caspase-8 (1:1000) and anti-cleaved caspase-3 (1:1000) were both from Cell Signaling, Danvers, Mass., USA. Enhanced chemiluminesce (ECL) Plus and ECL Prime western blotting detection kits were purchased from GE Healthcare, Pittsburgh, Pa., USA. Unless stated otherwise, all chemicals used were purchased from Sigma-Aldrich (St. Louis, Mo., USA) and were of the highest purity available.

DNA Constructs. Engineering of V5- and His-Tagged NMT1 and NMT2 Constructs.

NMT1 and NMT2 entry vectors which are compatible with the Gateway cloning system (Life Technologies, Grand Island, N.Y., USA) were purchased from Genecopoeia (Rockville, Md., USA). The NMT1 and NMT2 genes were incorporated into the destination vector pcDNA3.1/nV5 DEST (Life Technologies) using the LR clonase enzyme (Life Technologies) according to the manufacturer's instructions to generate the plasmids N-terminally-tagged NMTs (His-NMT1, His-NMT2, V5-NMT1 and V5-NMT2). V5-tagged NMT constructs were used for mammalian cell expression, whereas His-NMT constructs were used for bacterial expression. The cloning products were confirmed by DNA sequencing (Eurofins MWG Operon, Huntsville, Ala., USA).

Cell Culture.

Origin of the B cells were a gift from Dr. Jim Stone or were obtained from ATCC. All reagents from cell culture were purchased from Invitrogen. B cells were cultured at 37° C. and 5% $CO_2$ in a humidified incubator and maintained in RPMI media supplemented with 10% fetal bovine serum, 100 U/ml penicillin and 0.1 mg/ml streptomycin.

Cell Lysis.

Cells were washed in cold PBS, lysed in 0.1% SDS-RIPA buffer [50 mM Tris, 150 mM NaCl, 1% Igepal CA-630, 0.5% NaDC, 2 mM $MgCl_2$, and 1× complete protease inhibitor (Roche Diagnostics); pH 8.0] and rocked for 15 min at 4° C. Cell lysates supernatant were obtained after a 16,000 g centrifugation for 15 min at 4° C.

Induction of Apoptosis.

Unless mentioned otherwise, apoptosis was induced using 2.5 µM staurosporine (STS) (Sigma Aldrich, St. Louise, Mo., USA) and 5 µg/mL cycloheximide (ICN Biochemicals Inc. Aurora, Ohio, USA) in order to inhibit protein translation and enhance apoptosis induction.

Incubation with NMT Inhibitors.

Tris dibutylbenzinylidene acetone palladium (TrisDBA) was a kind gift of Dr. Arbiser. Cells were incubated at increasing concentrations for 24 hours with TrisDBA (or DMSO for control) or for 24 and 48 hours with DDD85646.

B Cell Transfection.

B cells were transfected using the Neon® transfection system (Life technologies) following manufacturer's instructions and optimized protocol for Ramos B cells transfection (pulse voltage 1,300V; pulse width 20 ms, 2 pulses and $7.7 \cdot 10^6$ cells/mL) adapted for 100 µL tips. Classically, two transfections were pulled to obtained enough living cells to perform a viability assay.

Cell Viability Assay.

B and T cell viability was measured using the trypan blue exclusion method. Cells were grown in confluency conditions ($2 \times 10^6$ cells/mL maximum) assuring the minimum basal apoptosis. After incubation with NMT inhibitors, about 20 000 cells (10 µL) were incubated with 10 µL of TC10™ Trypan Blue Dye (Biorad) for 15 min. Cell viability was quantified using the TC10™ automated cell counter (Biorad).

In Vitro NMT Activity Assay.

N-myristoyltransferase activity assay protocol was adapted from Raju, R. V., and Sharma, R. K. (1999) Preparation and assay of myristoyl-CoA:protein N-myristoyl-transferase. Methods Mol Biol 116, 193-211. [$^3$H] myristoyl-CoA was freshly synthesized for each experiment, as previously described by Towler, D., and Glaser. L. (1986) Protein fatty acid acylation: enzymatic synthesis of an N-myristoylglycyl peptide. Proc Natl Acad Sci USA 83, 2812-2816. Briefly, cells were resuspended in 0.25 M sucrose buffer (50 mM $NaH_2PO_4$, pH 7.4) and subjected to 2 rounds of sonication at level 6.0 on a Branson Sonicator. Reaction mixture is composed of 10 µL of cell extract (about 20 µg of proteins) incubated in NMT activity buffer (0.26M Tris-HCL, 3.25 mM EGTA, 2.92 mM EDTA and 29.25 mM 2-mercaptoethanol, 1% Triton X-100, pH 7.4) and myristoylable or non-myristoylable decapeptide corresponding to the N-terminal sequence of truncated-Bid (0.1 mM dissolved in water). Reaction was started by the addition of 7.4 µL (≈10 µMol) of freshly synthesized [$^3$H] myristoyl-CoA (final mixture volume=25 µL) and incubated for 15 min at 30° C. The reaction is stopped by spotting 15 µL of the reaction mixture on a P81 phosphocellulose paper disc (Whatman, Kent, UK) and dried for 30 seconds. Discs were washed (washing buffer: 25 mM Tris buffer, pH 7.4) to remove the residual radioactivity ([$^3$H]-myristate and [$^3$H]-myristoyl-CoA) while [$^3$H]-myristoyl-peptide is retained on the phosphocellulose paper. Radioactivity was quantified by liquid scintillation counting and converted into pMol of myristoylated peptide (Raju, R. V., and Sharma, R. K. (1999) Preparation and assay of myristoyl-CoA:protein N-myristoyltransferase. Methods Mol Biol 116, 193-211

RT-PCR.

qRT-PCR was performed with Taqman NMT1 and NMT2 probes using an 18S probe as an internal control. The difference in the number of cycle times (Δct) was calculated by subtracting the cycle time (ct) at which we see an exponential increase in the expression of the 18S internal control for each cell type from the NMT cycle time, again at a point where exponential increase of the signal is seen.

Example 1

FIG. 1 depicts the analysis of NMT1 and NMT2 expression in normal cells and various B cell lymphomas and T cell leukemias. This figure shows the near complete absence of expression of NMT2 in B Lymphoma cell lines (BL-2, Ramos), which express only NMT1 in comparison to normal B cells (EBV transformed human B lymphocytes, L0) and human leukemic T cell lines (Jurkat, MOLT-4, CEM).

While not wishing to be bound by theory, those cells which express only one NMT isozyme, for example Burkitt's lymphoma cells which shows the near complete absence of NMT2, are likely to have altered myristoylated protein profiles.

A sample which has a reduced amount myristoylated protein in a sample (optionally as compared to a control) is indicative of an NMT deficient sample, or NMT deficient cancer. Such an NMT deficient cancer is suitable to treatment with an inhibitor or NMT1.

Example 2

FIG. 2 depicts the sensitivity of various B cell lymphomas and T cell leukemias to the NMT inhibitors tris-dibenzylideneacetone-dipalladium (Tris-DBA). Various B and T cells were incubated for 24 h with increasing concentration of Tris DBA. Cell viability was measured using trypan blue exclusion method and adjusted to 100% for control. Cell survival curves measured by trypan blue exclusion show that B cell lymphomas are more sensitive to the NMT inhibitor tris-dibenzylideneacetone-dipalladium (Tris-DBA).

Example 3

Figure 3:
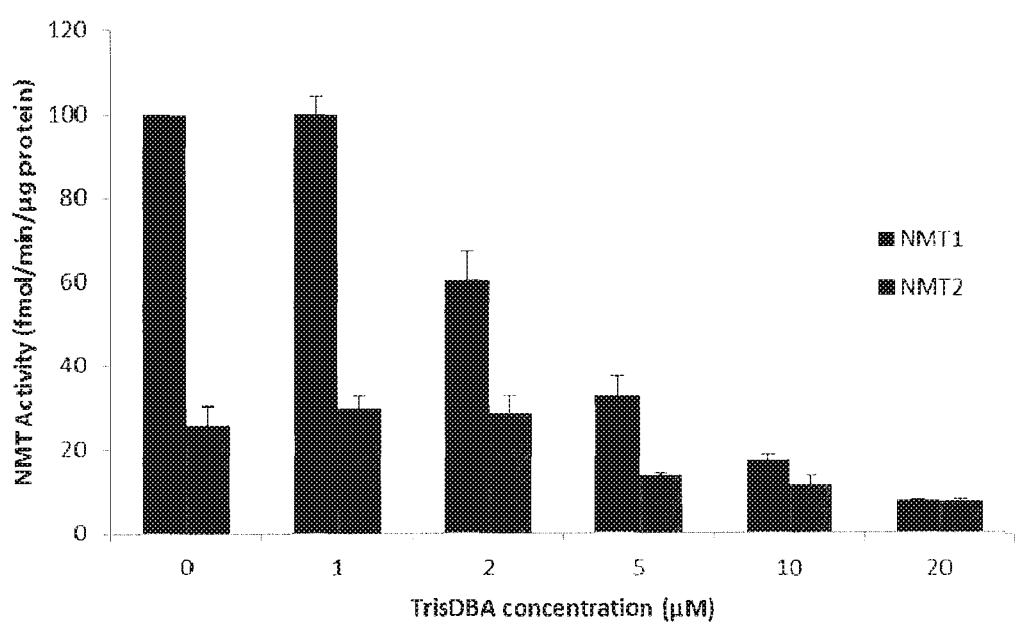
FIG. 3 is a bar graph illustrating inhibition of N-myristoyltransferase (NMT) by tris-dibenzylideneacetone-dipalladium (Tris-DBA)

FIG. 3 depicts the inhibition of N-myristoyltransferase (NMT) by tris-dibenzylideneacetone-dipalladium (Tris-DBA).

NMT activity was assayed using a peptide myristoylation assay with purified recombinant NMT1 and NMT2. NMT activity was calculated from the amount of radiolabeled myristoylpeptide produced and detected on phosphocellulose paper (adapted from King et al. 1991, Anal Biochem.).

This figure shows that tris-dibenzylideneacetone-dipalladium (Tris-DBA) inhibits NMT in vitro using purified recombinant NMTs enzymes.

Example 4

FIG. 4 depicts the results of immunoblots in which lymphoma cell lines were probed with antibodies against NMT 1 (Panel A) and NMT 2 (Panel B). The legend of FIG. 4 corresponds as follows: IM9: B lymphoblast; BL2: Burkitt's lymphoma; CEM: T cell leukemia; Karpas 299: T cell lymphoma; Sup-M2: ALCL; UCONN: ALCL (ALCL: Anaplastic large-cell lymphoma); DAUDI: Burkitt's lymphoma; Ramos: Burkitt's lymphoma BJAB: Burkitt's lymphoma; HD-MYZ: Hodgkin lymphoma; KM-H2: Hodgkin lymphoma; L428: Hodgkin lymphoma; Jurkat: T cell leukemia.

Example 5

FIG. 5 depicts the effectiveness of NMT inhibitors on Burkitt's Lymphoma cell line Ramos in comparison to immortalized normal B lymphocytic cell line (IM9) after 48 hours, at different concentrations.

Example 6

Figure 6:
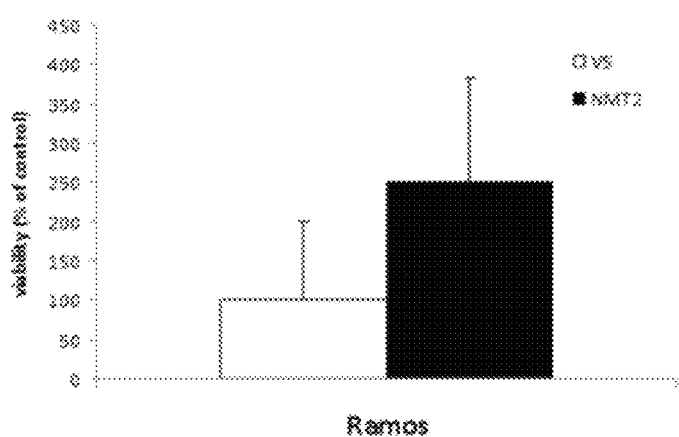
FIG. 6 depicts the results of transfection of Ramos B lymphoma cells with pcDNA3.1-V5-NMT2 showing increased survival to TrisDBA (5 ug/ml) 2.5 fold vs control cells transfected with empty plasmid vector (Panel A) showing cell viability, and (Panel B) an immunoblott.
Figure 6:
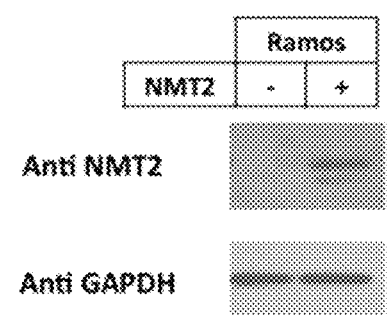

In this example, transfection of Ramos B lymphoma cells (which, as shown herein, expresses NMT1) with pcDNA3.1-V5-NMT2 increased survival to TrisDBA (5 ug/ml) 2.5 fold vs control cells transfected with empty plasmid vector. In FIG. 6, $20=10^6$ Ramos B lymphoma cells were transfected with 32 µg of DNA (pcDNA3.1-V5-empty or pcDNA3.1-V5-NMT2) using the Neon Transfection System (Invitrogen) following the recommended protocol for Ramos cell line (1,350 Volt, 30 ms). Transfected cells were centrifuged 5 minutes at 1200 rpm to remove dead cells and cellular debris. Cells in the supernatant were allowed to recover for 6 hours in complete RPMI. After a PBS wash, cells were resuspended and grown in RPMI containing TrisDBA (5 ug/ml) for 24 hours then counted using the trypan blue exclusion method (Panel A). Cells were lysed and western blotting (ECL) was performed to confirm expression NMT2 with antibodies against NMT2, and GAPDH for loading control (Panel B).

Example 7

In this example, qRT-PCR was performed with Taqman NMT1 and NMT2 probes using an 18S probe as an internal control. The difference in the number of cycle times (Δct) was calculated by subtracting the cycle time (ct) at which we see an exponential increase in the expression of the 18S internal control for each cell type from the NMT cycle time, again at a point where exponential increase of the signal is seen. As shown in Table 1, below, the ratio of NMT2 to NMT1 expression is decreased (up to 60 fold) in B lymphoma cell lines. While not wishing to be bound by theory, these results may suggest that that a reduction in mRNA encoding for NMT2 may be responsible for the reduction of NMT 2 protein levels assessed by Western blotting.

TABLE 1

Analysis of NMT mRNA expression by qRT-PCR

| | | mRNA sequence | Δct (ctNMT-ct18S) | NMT mRNA expression normalized to 18S | mRNA fold decrease of NMT2 vs NMT1 |
|---|---|---|---|---|---|
| Immortalized Normal B cell line | IM9 | NMT1 | 1.25 | 0.42 | 0.27 |
| | | NMT2 | 3.12 | 0.12 | |
| | L0 | NMT1 | 4.02 | 0.06 | 1.95 |
| | | NMT2 | 3.06 | 0.12 | |
| B cell lymphoma cell line | Ramos | NMT1 | −1.21 | 2.31 | 24.68 |
| | | NMT2 | 3.42 | 0.09 | |
| | BL2 | NMT1 | −0.088 | 1.06 | 60.41 |
| | | NMT2 | 5.83 | 0.02 | |

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The invention claimed is:

1. A method of treating a human subject having Burkitt's lymphoma that expresses an N-myristoyltransferase 1 (NMT1) protein and comprises a loss of N-myristoyltransferase 2 (NMT2) protein activity or level as compared to normal human B cells, comprising:

administering to said human subject a therapeutically effective amount of an inhibitor of NMT1 protein, wherein said NMT1 inhibitor inhibits NMT1 protein activity, wherein said NMT1 inhibitor is DDD85646, or a derivative thereof.

2. The method of claim 1, further comprising administering a chemotherapeutic agent to said human subject.

3. The method of claim 2, wherein said chemotherapeutic agent is CHOP, GAP-BOP, m-BACOD, ProMACE-MOPP, ProMACE-CytaBOM, MACOP-B, IMVP- 16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

4. A treatment method comprising administering DDD85646 or a derivative thereof to a human subject identified as having Burkitt's lymphoma that expresses an N-myristoyltransferase 1 (NMT1) protein and comprises a loss of N-myristoyltransferase 2 (NMT2) protein activity or level as compared to normal human B cells.

5. The method of claim 4, further comprising administering a chemotherapeutic agent to said human subject.

6. The method of claim 5, wherein said chemotherapeutic agent is CHOP, GAP-BOP, m-BACOD, ProMACE-MOPP, ProMACE-CytaBOM, MACOP-B, IMVP-16, MIME, DHAP, ESHAP, CEFF(B), CAMP, VABCD, ABDIC, CBVD, PCVP, CEP, EVA, MOPLACE, MIME, MINE, MTX-CHOP, CEM, CEVD, CAVP, EVAP, or EPOCH.

* * * * *